(12) United States Patent
Pawliszyn

(10) Patent No.: US 6,941,825 B2
(45) Date of Patent: Sep. 13, 2005

(54) ANALYTICAL DEVICES BASED ON DIFFUSION BOUNDARY LAYER CALIBRATION AND QUANTITATIVE SORPTION

(76) Inventor: Janusz B. Pawliszyn, 383 Dunvegan Dr., Waterloo, Ontario (CA), N2K 1W7

( * ) Notice: Subject to any disclaimer, the term of this patent is extended or adjusted under 35 U.S.C. 154(b) by 0 days.

(21) Appl. No.: 10/440,246

(22) Filed: May 19, 2003

(65) Prior Publication Data

US 2003/0200796 A1 Oct. 30, 2003

Related U.S. Application Data

(62) Division of application No. 09/771,649, filed on Jan. 30, 2001, now Pat. No. 6,588,255.
(60) Provisional application No. 60/179,755, filed on Feb. 2, 2000.

(51) Int. Cl.[7] .......................... G01N 30/04; G01N 30/16
(52) U.S. Cl. .................. 73/864.87; 73/31.07; 73/64.56; 73/863.21; 422/69; 436/178
(58) Field of Search ............................. 73/23.3, 23, 34, 73/24.01, 31.05, 31.07, 64.53, 64.56, 863.21, 863.87; 422/69; 436/178

(56) References Cited

U.S. PATENT DOCUMENTS

| | | | | |
|---|---|---|---|---|
| 3,195,346 A | * | 7/1965 | Ehrmantraut et al. | 73/53 |
| 3,318,138 A | * | 5/1967 | Rolfson | 73/64.3 |
| 4,028,931 A | * | 6/1977 | Bisera et al. | 73/64.3 |
| 4,245,495 A | * | 1/1981 | Kakiuchi et al. | 73/643 |
| 4,488,814 A | * | 12/1984 | Johnson | 356/414 |
| 4,732,046 A | * | 3/1988 | Lawrence et al. | 73/864.21 |
| 4,751,004 A | * | 6/1988 | Stevens et al. | 210/659 |
| 4,860,577 A | * | 8/1989 | Patterson | 73/64.3 |
| 4,863,696 A | * | 9/1989 | Saydek et al. | 422/101 |
| 5,065,614 A | * | 11/1991 | Hartman et al. | 73/23.35 |
| 5,141,873 A | * | 8/1992 | Steudle et al. | 436/148 |
| 5,198,109 A | * | 3/1993 | Hanson et al. | 210/321.75 |
| 5,432,098 A | * | 7/1995 | Wilks | 436/178 |
| 5,565,622 A | * | 10/1996 | Murphy | 73/61.55 |
| 5,591,636 A | * | 1/1997 | Grass | 435/287.1 |
| 5,691,206 A | * | 11/1997 | Pawliszyn | 436/178 |
| 5,693,228 A | * | 12/1997 | Koehler et al. | 210/656 |
| 5,723,769 A | * | 3/1998 | Barber et al. | 73/19.12 |
| 5,804,743 A | * | 9/1998 | Vroblesky et al. | 73/863.23 |
| 5,889,195 A | * | 3/1999 | Kaneblei | 73/19.12 |
| 5,906,747 A | * | 5/1999 | Coffman et al. | 210/635 |
| 5,942,440 A | * | 8/1999 | Dooley et al. | 436/146 |
| 5,979,219 A | * | 11/1999 | Sellmer-Wilsberg et al. | 73/19.12 |

(Continued)

FOREIGN PATENT DOCUMENTS

| | | | | |
|---|---|---|---|---|
| EP | 75371 A1 | * | 3/1983 | G01N/31/08 |
| JP | 2002-110991 A | * | 4/2002 | |
| WO | WO 9841855 A1 | * | 9/1998 | G01N/30/18 |
| WO | WO 9931480 A1 | * | 6/1999 | G01N/1/34 |

OTHER PUBLICATIONS

ManI,et al, Applications of Solid Phase Microectraction, RSC, Cornwall, U.K., 1999, Chapter 5, p. 57–72.

(Continued)

Primary Examiner—Hezron Williams
Assistant Examiner—David A. Rogers

(57) ABSTRACT

A method and device for determining the concentration of analytes in a sample. The device has a surface with an extraction coating thereon. The method is carried out while the sample is highly agitated to maintain a substantially constant boundary layer. The sample is brought into contact with the coating for a limited time so that all the analytes that pass through the boundary layer are adsorbed by the coating. The amount of analytes in the coating is determined and the concentration of those same analytes in the sample is then calculated from the diffusion coefficient of the analytes. The device is first calibrated using analytes of known concentration.

26 Claims, 20 Drawing Sheets

U.S. PATENT DOCUMENTS

| | | | | |
|---|---|---|---|---|
| 6,042,787 A | * | 3/2000 | Pawliszyn | 422/69 |
| 6,076,395 A | * | 6/2000 | Black et al. | 73/64.47 |
| 6,119,506 A | * | 9/2000 | Gibson et al. | 73/38 |
| 6,131,440 A | * | 10/2000 | Bertrand | 73/23.39 |
| 6,164,144 A | * | 12/2000 | Berg | 73/863.21 |
| 6,269,679 B1 | * | 8/2001 | McCarthy et al. | 73/19.1 |
| 6,272,906 B1 | * | 8/2001 | Fleury et al. | 73/64.55 |
| 6,360,588 B1 | * | 3/2002 | Ross et al. | 73/38 |
| 6,376,255 B1 | * | 4/2002 | Schwab et al. | 436/177 |
| 6,541,272 B1 | * | 4/2003 | Mitra | 436/178 |

OTHER PUBLICATIONS

Martos, e al., "Calibration of SPME for Air Analyses Based on Physical Chemical Properties of the Coating" Analytical Chemistry, 1997, 69, p. 206–15.

Chai, et al., "Determination of Volatile Chlorinated Hydrocarbons in Air and Water with Solid Phase Microextraction" Analyst, 1993, 118, p. 1501–1505.

Martos, et al., "Estimation of Air/Coating Distribution Coefficients for SPME Using LTPRI Capillary GC" Analytical Chemistry, 1997, 69, p. 402–8.

Grote, et al., "Solid Phase Microextraction for the Analysis of Human Breath" Analytical Chemistry, 1997, 69, p. 587–596.

Koziel, et al., "Field Air Analysis with SPME Device" Analytica Chimica Acta, 1999, 400, p. 153–162.

Gorecki, Applications of Solid Phase Microextraction, RSC, Cornwall, UK, 1999, Chapter 7, p. 92–108.

Ai, Applications of Solid Phase Microextration, RSC, Cornwall, UK, 1999, Chapter 2, p. 22–37.

Cooper, Air Pollution Control: A Design Approach, Waveland Press Inc., Prospect Heights, 1994, Chapter 13, p. 411–447.

Pawliszyn, Solid Phase Microextraction: Theory and Practice, Wiley/VCH, Inc., New York, 1997.

Lugg, "Diffusion Coefficients of Some Organic and Other Vapors in Air" Analytical Chemistry, 1968, 40, p. 1072–1077.

Tucker et al., Handbook of Chemical Property Estimation Method, ACS, McGraw–Hill, Inc., New York, 1982, Chapter 17, p. 17.0–17.25.

* cited by examiner

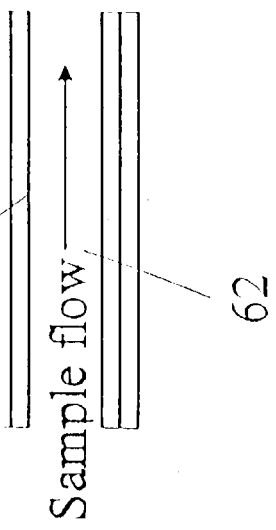
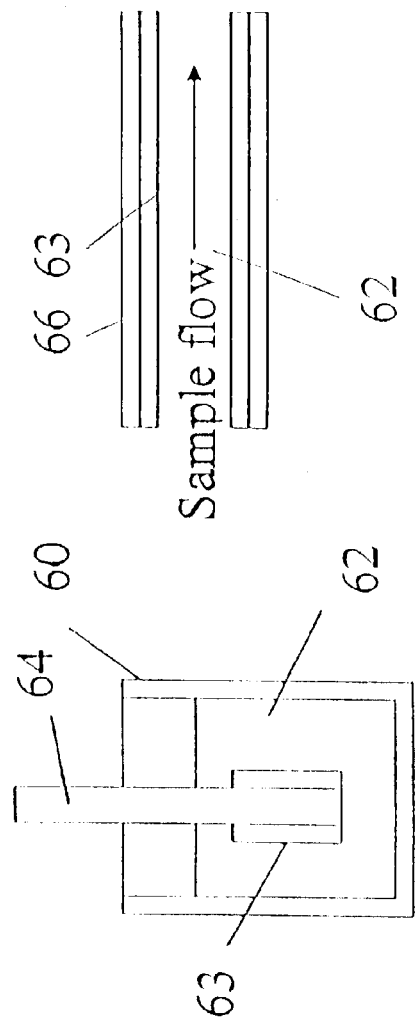
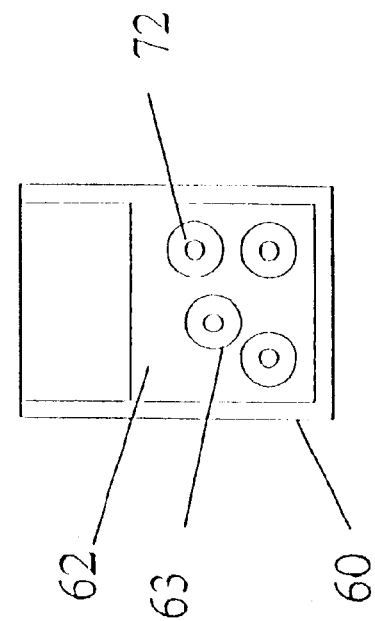
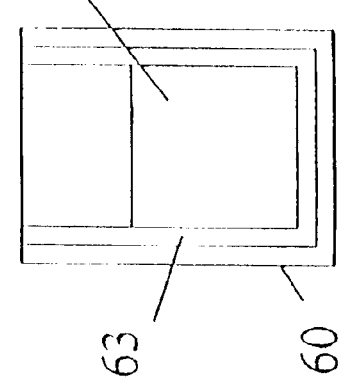

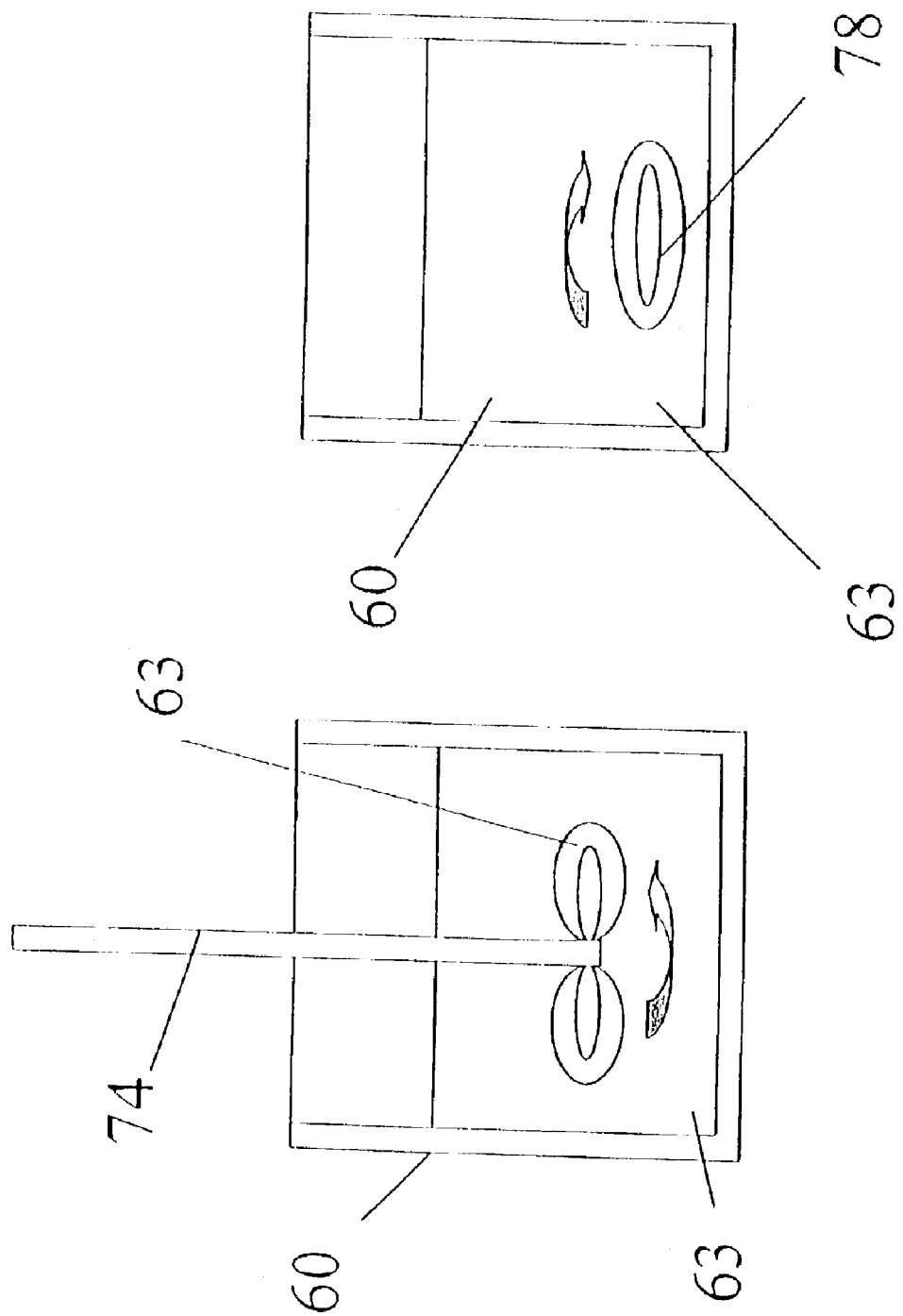

ANALYTICAL DEVICES BASED ON DIFFUSION BOUNDARY LAYER CALIBRATION AND QUANTITATIVE SORPTION

This application is a divisional application of application Ser. No. 09/771,649 filed on Jan. 30, 2001 now U.S. Pat. No. 6,588,255.

This application also claims the benefit of provisional application No. 60/179,755 filed Feb. 2, 2000.

BACKGROUND OF THE INVENTION

1. Field of the Invention

This invention relates to a method and device of determining the concentration of analytes in sample using an extraction device whereby the concentration of analytes of interest can be determined from the diffusion coefficient for said analytes. More particularly, this invention relates to a method and device for determining the concentration of organic and inorganic compounds in liquid and gaseous samples.

2. Description of the Prior Art

It is known to use solid phase microextraction (SPME) and polydimethylsiloxane (PDMS) coated fibers to extract volatile organic compounds (VOC's) in environmental samples. PDMS is the most widely used coating for extracting nonpolar volatile analytes as well as many polar analytes. However, the sensitivity of mixed phase SPME coatings, such as PDMS/DVB and Carboxen/PDMS was reported to be much higher compared to PDMS coating for extracting VOC's (see Mani et al, Applications of Solid Phase Microextraction, RSC, Cornwall, U.K., 1999, Chapter 5). Mixed phase coatings have some complementary properties compared to PDMS and are more suitable for sampling highly volatile species (see Pawliszyn, Solid-Phase Microextraction: Theory and Practice, Wiley-VCH, Inc., New York, 1997, Chapter 4). Mixed phase SPME fibers have been used for sampling and quantifying target VOC's present in indoor air at the part per billion level and even at the part per trillium level.

Indoor air quality and its potential impact on human health is an increased concern to the public and government environmental agencies. Many VOC's, such as formaldehyde, aromatic compounds, and halogenated hydrocarbons have been found to be highly toxic to humans. Large-scale air quality testing by conventional air sampling methods can often be time-consuming and expensive. Solid phase microextraction coupled with gas chromatography has been previously successfully applied to analyze various air samples. Chai et al., Analyst, 1993, 118,1501 reported the determination of the presence of volatile chlorinated hydrocarbons in air by SPME in 1993. Martos et al. developed a new method using a linear temperature-programmed retention index method to calibrate SPME devices for fluctuations in sampling temperature, and for air analysis of total VOC's with (PDMS) fibers (see Martos et al., Analytical Chemistry, 1997, 69, 206 and 402). Grote et al used SPME for fast quantitative analysis of acetone, isoprene and ethanol in human breath with SPME fibers in Analytical Chemistry, 1997, 69, 587. It is known that the syringe-like SPME device is portable and can be easily used for field analysis. When coupled with a field-portable gas chromatograph, both SPME sampling and instrumental analysis can be conducted at the test site without the need for sample preservation (see Koziel et al, Analytical Chemistry, Acta, 1999, 400(1–3), 153.

In mixed phase coatings, the majority of interaction on porous polymer particles is determined by the adsorption process. With mixed phase coatings, the molecules can be attracted to a solid surface via van der Waals, dipole-dipole, and other weak intermolecular forces (see Górecki et al, Applications of Solid Phase Microextraction, RSC, Cornwall, UK, 1999, Chapter 7). Hydrophobic interaction and electrostatic interaction also occur when extracting analytes from water and ionizable analytes from aqueous phase, respectively. Compared to the diffusion coefficient in liquid coatings of PDMS or PA, the diffusion coefficients of VOC's in divinylbenzene and Carboxen are so small that, within the frame of SPME analysis, essentially all the molecules remain on the surface of the coating. Therefore, the fundamental difference between adsorption and absorption is that in adsorption molecules bind directly to the surface of a solid phase while, in absorption, they dissolve into the bulk of the liquid phase.

The Langmuir adsorption isotherm is one of most important adsorption theories. The Langmuir model assumes there is only a limited number of surface sites that can be occupied by analyte molecules, all sites are equivalent, and there is no interaction between absorbate molecules on adjacent sites. The Langmuir adsorption isotherm was used to describe the adsorption equilibrium on PDMS/DVB and Carbowax/DVB coatings. A linear function is found to exist only if the affinity of an analyte toward the coating is low or its concentration in the sample is very low. In a real sample matrix, for example, air, there are usually more than two components. Since different components have different affinities towards the active sites, the presence of multi-components must affect the adsorption of one other. Unlike the non-competitive absorption process in liquid coatings, adsorption process onto porous polymer coatings in a multi-component system is a competitive process and therefore displacement effect is expected. Sampling conditions, the sample matrix composition and concentration can largely affect the amount of analytes extracted by mixed phase fibers. From a practical point of view, this makes quantitative analysis using porous polymer SPME coatings more difficult.

The majority of adsorption models are based on the equilibrium theory. In SPME, however, the equilibrium time ranges from a few minutes to a couple of hours depending on the nature of the analytes and the sampling conditions (see Ai et al., Applications of Solid Phase Microextraction, RSC, Cornwall, UK, 1999, Chapter 2). For porous solid coatings, the equilibrium time for the same analyte is usually much longer than that in liquid coatings. It may be impractical to wait for partition equilibrium of all of analytes in the matrix if the equilibrium times for some analytes are too long.

In the direct SPME system, such as sampling in air or in water, the analyte movement proceeds in two steps. The first step consists of the mass transfer of analytes from the bulk sample matrix to the surface to the SPME polymer coating followed by diffusion of the analytes within the coating. Fick's first law of diffusion (equation 1) can describe the rate of mass diffusion in the sample matrix in the coating as follows:

$$F = -D_s \left( \frac{\partial C_s}{\partial x} \right) \qquad \text{(eq. 1)}$$

Where F is the flux of analyte in the direction x from the sample matrix bulk to the SPME fiber surface.

(i) $D_s$ is the diffusion coefficient of the analyte in the sample matrix, (ii) $C_s$ is the analyte concentration in the sample bulk.

In a static gas system, mass movement results only from molecular diffusion due to intermolecular collisions. In practice, both molecular diffusion and bulk fluid movement must be considered. The extent of fluid movement (agitation), reflects the access of analytes to the surface and is frequently described as a theoretical parameter called the boundary layer (Cooper et al, Air Pollution Control: A Design Approach, Waveland Press Inc., Prospect Heights, 1994, Chapter 13).

According to the boundary layer theory, a laminar sublayer or the sample matrix film is formed when a fluid passes a fixed object. The only way that the analyte can pass from the air bulk phase to the surface of the coating is via molecular diffusion across the boundary layer. In the liquid/solid interface, the thickness of the boundary layer is determined by the agitation conditions and the viscosity of the fluid (see Pawliszyn, Solid Phase Microextraction: Theory and Practice, Wiley/VCH, Inc., New York, 1997).

In a gas system, air wind velocity is a very important factor in mass transfer process. Because the value of wind velocity represents the degree of bulk air movement, wind velocity will influence the overall mass transfer rate in the bulk of fluid. Based on mass transfer theories, the mass transfer rate of an analyte is proportional to the mass diffusivity, and inversely proportional to the thickness of gas film at the interface.

Many factors such as temperature, pressure, molecular structure and molecular weight can directly affect the molecular diffusion coefficients of VOC's (see Lugg, G. A., Analytical Chemistry, 1968, 40 (7), 1072). Since accurate experimental measurement of the diffusion coefficient is difficult, relatively few values for organic compounds in gas systems are available from the literature. A number of methods have been proposed for estimation of diffusion coefficients of VOC's in air systems. The method by Fuller, Schettler and Giddings (FSG method) was reported to be most accurate for non-polar organic gases at low to moderate temperature (see Lyman et al, Handbook of Chemical Property Estimation Method, ACS, McGraw-Hill, Inc., New York, 1982, Chapter 17). Minimal error is associated with the aliphatics and aromatics. FSG model describes that the molecular diffusion coefficient of an analyte is directly proportional to temperature, and inversely proportioned to air pressure. The relative humidity of air is another factor that can affect VOC extraction on SPME fibers because water molecules participate in the adsorption process.

SUMMARY OF THE INVENTION

A method of determining a concentration of analytes of interest in a sample using a solid phase microextraction device having a surface containing an extraction coating comprises bringing the sample into contact with the coating while highly agitating the sample under controlled conditions to maintain a substantially constant boundary layer between the sample and the coating. The method further comprises limiting a time of contact between the sample and the coating and sizing the coating so that all analytes that pass through the boundary layer are adsorbed by the coating. The method further comprises terminating the contact, determining the amount of each analyte of interest in the coating and calculating the concentration of each analyte of interest in the sample by using the diffusion coefficient for that analyte.

A method of determining the concentration of analytes of interest in a sample uses an extraction device having a membrane. The method comprises bringing the sample into contact with the membrane for sufficient time to allow microextraction to occur. The method further comprises choosing a membrane with a large surface area and limiting the time of contact so that all analytes that contact the membrane are adsorbed by the membrane. The method further comprises separating the membrane from the sample, determining the amount of each analyte of interest in the membrane and calculating the concentration of each analyte of interest in the sample using the diffusion coefficient for that analyte.

A device for determining the concentration of analytes of interest in a sample, the device comprises a solid phase microextraction device having a surface containing an extraction coating characterized by a large surface area to adsorb all analytes that contact said coating and agitation means to highly agitate the sample under controlled conditions during microextraction.

In a further embodiment, a device for determining the concentration of analytes of interest in a sample uses a membrane having a large surface area to adsorb all analytes that contact a surface of the membrane in a time allowed for extraction. The membrane is sized and shaped to fit into an injection port of an analytical instrument.

BRIEF DESCRIPTION OF THE DRAWINGS

FIG. 15A is a schematic side view of an extraction device having a fiber with an extraction coating thereon;

FIG. 15B is a schematic side view of a flow tube having an extraction coating on an inner surface thereof;

FIG. 15C is a schematic side view of a vessel having an extraction coating on an interior surface of the vessel;

FIG. 15D is a schematic side view of a vessel containing particulates with an extraction coating thereon;

FIG. 15E is a schematic side view of a vessel having a stirrer with an extraction coating on the stirrer;

FIG. 15F is a schematic side view of a vessel having a stirring bar with an extraction coating on said bar;

DESCRIPTION OF A PREFERRED EMBODIMENT

Figure 1:
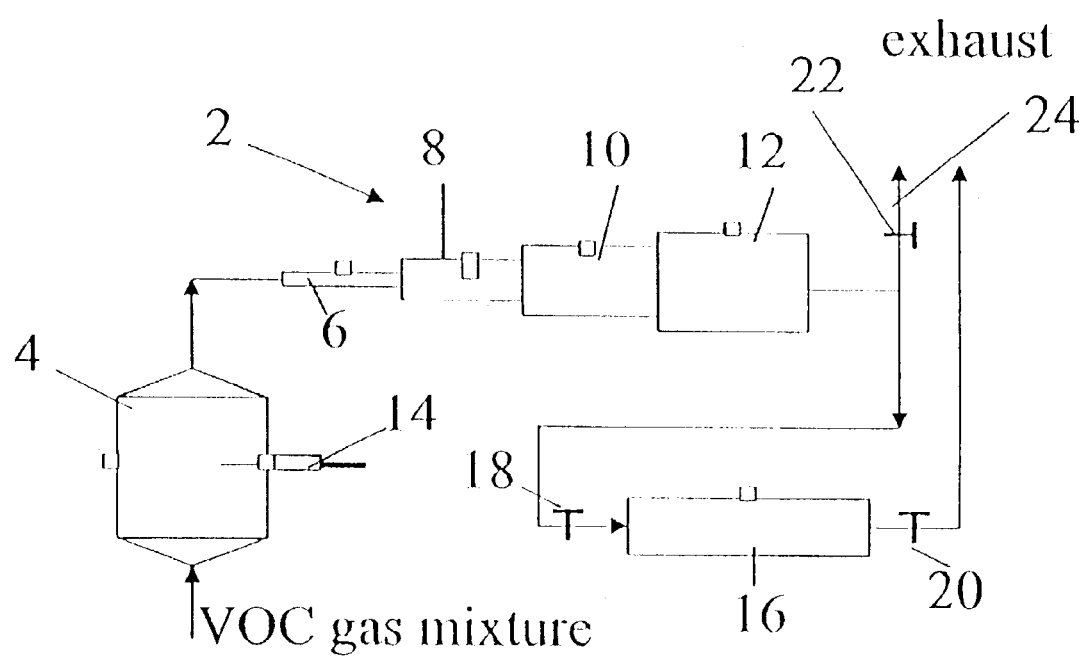
FIG. 1 is a flow diagram of an air sampling system.

Compared to the diffusion coefficient and liquid coatings of PDMS or PA, the diffusion coefficients of VOC's in divinylbenzene and Carboxen are so small that, with the frame of SPME analysis, essentially all of the molecules remain on the surface of the coating. Sampling conditions, the sample matrix composition and concentration can largely effect the amount of analytes extracted by mixed phase fibers. From a practical point of view, this makes quantitative analysis using porous polymer SPME coatings more difficult.

It has been found that with a very short exposure time (for example, one minute), when using SPME with PDMS/DVB coating fibers for fast sampling and analysis of VOC's in indoor air, there is a linear relationship between adsorption and concentration. Within a one minute sampling period, airborne benzene, toluene, ethylbenzene and p-xylene (BTEX) extracted on a PDMS/DVB fiber increased linearly with the sampling time. The short exposure time before equilibrium produces an advantage due to the fact that the adsorption rate is controlled by diffusion coefficients of analytes rather than their distribution constants. Because the differences between the diffusion coefficients of VOC's are much smaller compared to the differences of the distribution constants are much smaller than the differences between the distribution constants, all target VOC's with similar molecular weights produce similar extraction rates when using a short sampling time.

The mass transfer parameters through a boundary layer should include both molecular diffusion and bulk fluid movement. When using a porous polymer SPME coating for air sampling, it can be reasonably assumed that all available analyte molecules are mobilized within a very short exposure period. In other words, when the concentration of analyte on the coating surface is far from the saturation point, all of the target molecules are immediately adsorbed as soon as they contact the surface of the porous solid extraction coating. If the matrix composition and sampling conditions are kept constant, it has been found that the rate of mass diffusion of analyte will be proportional to its mass diffusion coefficient in the sample bulk within this short time period. Also, it has been found that there exists a quantitative relationship between the amount of analytes adsorbed and concentration depending on the diffusion coefficient of analytes when using a very short exposure time that occurs well before equilibrium.

In the gas-solid interface, the thickness of the gas film is largely affected by the air movement or by the wind velocity and the nature of air. In a gas system, air wind velocity is a very important factor in the mass transfer process. Since the value of wind velocity represents the degree of bulk air movement, wind velocity will influence overall mass transfer rate in the bulk of the fluid. Based on mass transfer theories, the mass transfer rate of an analyte is proportional to the mass diffusivity and inversely proportional to the thickness of the gas film at the interface. Therefore, when considering air sampling with porous SPME fibers, air wind velocity is a very important factor related to the adsorption process, especially for pre-equilibrium extraction.

With the present invention, some of the critical factors, including air/wind velocity, sampling temperature and air relative humidity have been investigated in relation to the adsorption process of VOC's onto porous polymer SPME coatings under non-equilibrium conditions.

Extraction Model Development. The solid SPME fiber coating can be modeled as a long cylinder with length L, and outside and inside diameters of b and a, respectively (FIG. 1). When the coating is exposed to moving air, an interface (or boundary layer) with thickness $\delta$ develops between the bulk of air and the idealized surface of the fiber. The analytes are transported from the bulk air to the surface of the coating via molecular diffusion across the boundary layer. In most cases, the molecular diffusion of analytes across the interface is the rate-limiting step in the whole adsorption process.

The analyte concentration in the bulk air ($C_g$) can be considered constant when a short sampling time is used, and there is a constant supply of an analyte via convection. These assumptions are true for most cases of SPME air sampling, where the volume of air is much greater then than the volume of the interface, and the extraction process does not affect the bulk air concentration. In addition, the SPME solid coating can be treated as a perfect sink. The adsorption binding is instantaneous and the analyte concentration on the coating surface ($C_0$) is far from saturation and can be assumed to be negligible for short sampling times and relatively low analyte concentrations in a typical air. These concentrations range from parts-per-trillion (by volume) to parts-per-million (by volume) for most VOCs of interest and typical industrial hygiene, indoor and ambient air concentrations. The analyte concentration profile can be assumed to be linear from $C_g$ to $C_0$. In addition, the initial analyte concentration on the coating surface ($C_0$) can be assumed to be equal to zero when extraction begins. Diffusion inside the pores of a solid coating controls mass transfer from b to a.

The mass of extracted analyte with sampling time can be derived using the analogy of heat transfer in a cylinder with inside and outside diameters of b and $\delta$, respectively, with a constant axial supply of heat. The steady-state solution to heat transfer can be translated into a mass transfer solution by replacing temperatures with concentrations, heat with flux of mass and heat transfer coefficient with gas-phase molecular diffusion coefficient. As a result, the mass of extracted analyte can be estimated from the following equation:

$$n(t) = \frac{2\pi D_g L}{\ln\left(\frac{b+\delta}{b}\right)} \int_0^t C_g(t) dt \qquad (1)$$

where: n is the mass of extracted analyte over sampling time (t) in ng; $D_g$ is the gas-phase molecular diffusion coefficient (cm2/s); b is the outside radius of the fiber coating (cm); L is the length of the coated rod (cm); $\delta$ is the thickness of the boundary layer surrounding the fiber coating (cm); and $C_g$ is analyte concentration in the bulk air (ng/mL). It can be assumed that the analyte concentration is constant for very short sampling times and therefore Equation 1 can be further reduced to:

$$n(t) = \frac{2\pi D_g L}{\ln\left(\frac{b+\delta}{b}\right)} C_g t \quad (2)$$

where t is the sampling time (s). The fiber length and the outside diameter of the fiber coating are constant for each type of the fiber. The nominal length for the 65 μm PDMS/DVB and the 75 μm Carboxen™/PDMS coatings is L=1 cm, and the outside diameter 2b=0.0240 cm (±10%) and 2b=0.0260 cm (±10%), respectively.

It can be seen from Equation 2 that the amount of extracted mass is proportional to the sampling time, Dg for each analyte, bulk air concentration, and inversely proportional to δ. This in turn allows for quantitative air analysis. Equation 2 can be modified to estimate the analyte concentration in the air in ng/mL for rapid sampling with solid SPME coatings:

$$C_g = \frac{n \ln\left(\frac{b+\delta}{b}\right)}{2\pi D_g L t} \quad (3)$$

The amount of extracted analyte (n) can be estimated from the detector response.

For a special case, where the thickness of the boundary layer is much smaller than the outside radius of the fiber (δ<<b), the general solution can be reduced to a flat plate problem. For such condition, $\ln(1+\delta/b) \approx \delta/b$, $2\pi b L = A$, and Equation 2 simplifies to:

$$n(t) = \frac{D_g A}{\delta} C_g t \quad (4)$$

where A is the surface area of the sorbent. Equation 4 is analogous to the mass uptake model for the TWA sampling with retracted SPME fiber, where the distance between the needle opening and the fiber (Z) is replaced by δ.11,12.

Under equal conditions, the amount of extracted mass will be greater for an analyte with a greater gas-phase molecular diffusion coefficient (Dg). This is consistent with the fact that the analyte with a greater Dg will cross the interface and reach the surface of the fiber coating faster. Values of Dg for each analyte can be found in the literature or estimated from physicochemical properties. A number of methods have been proposed for estimation of diffusion coefficients of VOCs in air systems. The method by Fuller, Schettler and Giddings (FSG) was reported to be the most accurate for non-polar organic gases at low to moderate temperatures:

$$D_g = \frac{0.001 \times T^{1.75} \times \sqrt{\frac{1}{M_{air}} + \frac{1}{M_{voc}}}}{p\left[(\sum v_{air})^{\frac{1}{3}} + (\sum v_{voc})^{\frac{1}{3}}\right]^2} \quad (5)$$

where Dg is expressed in cm2/s; T is the absolute temperature (K); Mair, Mvoc are molecular weights for air and VOC of interest (g/mol); p is the absolute pressure (atm); Vair, Vvoc are the molar volumes of air and the VOC of interest (cm3/mol). According to the FSG model, Dg is directly proportional to temperature and inversely proportional to air pressure. Because the atmospheric pressure changes are relatively low, the air temperature is a more important factor than pressure when considering air sampling. Regardless, both atmospheric pressure and air temperature are routinely monitored during conventional air sampling.

The thickness of the boundary layer (δ) is a function of sampling conditions. The most important factors affecting δ are SPME coating radius, air velocity, air temperature and Dg for each analyte. The effective thickness of the boundary layer is determined by both rate of convection and diffusion. As the analyte approaches the sorbent surface, the overall flux is increasingly more dependent of diffusion than convection. The analyte flux in the bulk sample is assumed to be controlled by convection, whereas the analyte flux inside the boundary layer region is assumed to be controlled by diffusion. The effective thickness of the boundary layer can be described as the location where this transition occurs, i.e., where the flux towards δ (controlled by convection) is equal to the flux towards the surface of the SPME coating (controlled by diffusion). In the Nernst model, the matrix within the boundary layer is stationary. Experimental research indicated that convection was also present inside the boundary layer. However, its effects decreased with the distance to the solid surface. The effective thickness of the boundary layer can be estimated using Equation 6, adapted from the heat transfer theory for an SPME fiber in a cross flow:

$$\delta = 9.52 \frac{b}{Re^{0.62} Sc^{0.38}} \quad (6)$$

where Re is the Reynolds number=2ub/v, u is the linear air velocity (cm/s); v is the kinematic viscosity for air (cm²/s); Sc is the Schmidt number=v/D$_g$. The effective thickness of the boundary layer in Equation 6 is a surrogate (or average) estimate and does not take into account changes of the thickness that may occur when the flow separates and/or a wake is formed. Equation 6 indicates that the thickness of the boundary layer will decrease with an increase of the linear air velocity. Similarly, when air temperature (T$_g$) increases, the kinematic viscosity also increases. Since the kinematic viscosity term is present in the numerator of Re and in the denominator of Sc, the overall effect on δ is small.

The gas-phase molecular diffusion coefficient (D$_g$) for each analyte is also an important parameter controlling δ. As illustrated in Equation 6, the effective thickness of the boundary layer will be reduced for analytes with lower D$_g$. This can be explained considering that, analytes with low molecular weight will reach the coating surface faster then the less volatile analytes under equal experimental conditions and therefore the point at which the diffusion is a primary mode of analyte transport to the coating is located further away from the surface. The reduction of the boundary layer and the increase of the mass transfer rate for an analyte can be achieved in at least two ways, i.e., by increasing the air velocity and by increasing the air temperature. However, the temperature increase will reduce the solid sorbent efficiency. As a result, the sorbent coating may not behave as a zero sink for all analytes.

Chemicals and Supplies. The volatile organic compounds under study, i.e., benzene, toluene and p-xylenes were purchased from Sigma-Aldrich (Mississauga, ON). All VOC standards had purities≧98.0% and used for calibrating GC/FID response factors. National Institute of Standards and Technology (NIST) traceable certified permeation tubes of benzene, toluene and p-xylene were purchased from Kin-Tech (La Marque, Tex.), and used for the generation of a standard gas mixture. Ultrahigh purity hydrogen, nitrogen, air were purchased from Praxair (Waterloo, ON). SPME fibers with 65 μm PDMS/DVB, 75μm Carboxen/PDMS and SPME holders were purchased from Supelco (Oakville, ON).

Standard Gas. A standard gas-generating device with a flow-through sampling chamber, was constructed to provide a wide range of target VOC concentrations at constant temperature. Ultrahigh purity air (zero gas) was supplied from a Whatman air generator (Haverhill, Mass.) and maintained at 50 psi head pressure. Permeation tubes of benzene, toluene and p-xylene were held inside a glass permeation tube adapter (Kin-Tech, La Marque, Tex.) and swept with a constant flow of dilution air. The adapter was placed inside a cylindrical aluminum oven, which was heated by two heating elements (100 W), and its temperature was controlled by K-type thermocouple (Omega™, Stamford, Conn.) and an electronic heat control device (Science Shops, the University of Waterloo, ON). The air flow rate was controlled by two Sidetrack™ mass flow controllers (Sierra Instruments, Monterey, Calif.) placed on both the primary and the dilution loops in the system. Wide ranges of concentration for target VOC's were obtained by adjusting both the air flow rate and the permeation tube incubating temperature.

Design for Air Wind Velocity Study. As shown in FIG. 1, an air sampling system 2 consists of a main cylindrical glass chamber 4 and four additional cylindrical glass chambers 6, 8, 10, 12. All of the glass chambers 4, 6, 8, 10, 12 have different diameters with the chamber 4 being the largest. The chamber 6 has the smallest diameter with the chambers 8, 10, 12 each increasing in diameter in chronological order. The main chamber 4 contains an SPME device 14, which is described in more detail subsequently. A 1.0 L glass sampling bulb 16 (Supelco, Oakville, ON), was constructed and installed downstream from the standard gas generator. The gas flow rate varied from 1,000 standard cubic centimeters per minute (sccm) to 4,000 sccm for generating a wide range of air wind velocities. This new sampling system can provide both a dynamic airflow with different wind velocities and a static gas mixture. Experiments for estimation of the range of air velocities in typical indoor environments were conducted in a mechanically ventilated building using an OMEGA™ HHF51 Temperature and Air Velocity Meter (OMEGA, Stamford, Conn.). The indoor air velocities were found to vary with the distance between the measured location and the air vent, which is shown in the Table 1. The average indoor air velocity varied from 0 to 10 cm/s, and the average wind velocity at ventilating zones (near vent) varied from 15 to 40 cm/s. The data listed in Table 1 were consistent with the values reported by Wasiolek et al. (1999) Indoor Air-International Journal Indoor Air Quality and Climate, 9 (2) 125, who found that the average indoor wind velocities (at 19 locations in a workroom) varying from 1.4 to 9.7 cm/s, and the average wind velocity at the breathing-zone height varying from 9.9 to 35.5 cm/s by using an accurate three-dimensional sonic anemometer. The glass chambers 4, 6, 8, 10, 12 allowed for sampling under dynamic flow conditions, and the chamber 16 allowed for static sampling when stopcocks 18 and 20 were closed. A stopcock 22 opens and closes an exhaust line 24. The average wind velocities were calculated by dividing the airflow rate by the cross-section area of gas sampling chambers. When the air flow rate was set at 1,000 sccm, the air velocities ranged from 0.2 to 20.8 cm/s. When the air flow rate was increased to 4,000 sccm, the air velocities ranged from 0.8 to 83.2 cm/s. Since the Reynolds numbers in all chambers were less than 1,200, the air flow in the sampling chambers was in a laminar flow condition. A 65 μm PDMS/DVB fiber was used to sample the VOC gas mixture in each sampling port under different average air velocities. A short exposure time of 20 seconds was used to examine the effect of wind velocity on the VOC adsorption process onto PDMS/DVB fiber. The extraction time profiles of airborne BTEX were also constructed under various wind velocities.

Design for Temperature Study. The gas flow rate was maintained at 1,000 sccm, and the permeation tubes were incubated at 60° C. The main sampling chamber 4 in FIG. 1 was used to provide a steady-state mass flow of VOC's at different temperatures. The air temperature in the vicinity of the SPME fibers was maintained within ±0.3° C. at the range of room temperature. A 65 μm PDMS/DVB fiber and a 75 μm Carboxen/PDMS fiber were used to sample the VOC gas mixture in the chamber. The temperature of the air stream in the chamber varied from 22 to 40° C. The SPME fiber exposure times were 5 seconds and 10 seconds, respectively.

Figure 2:
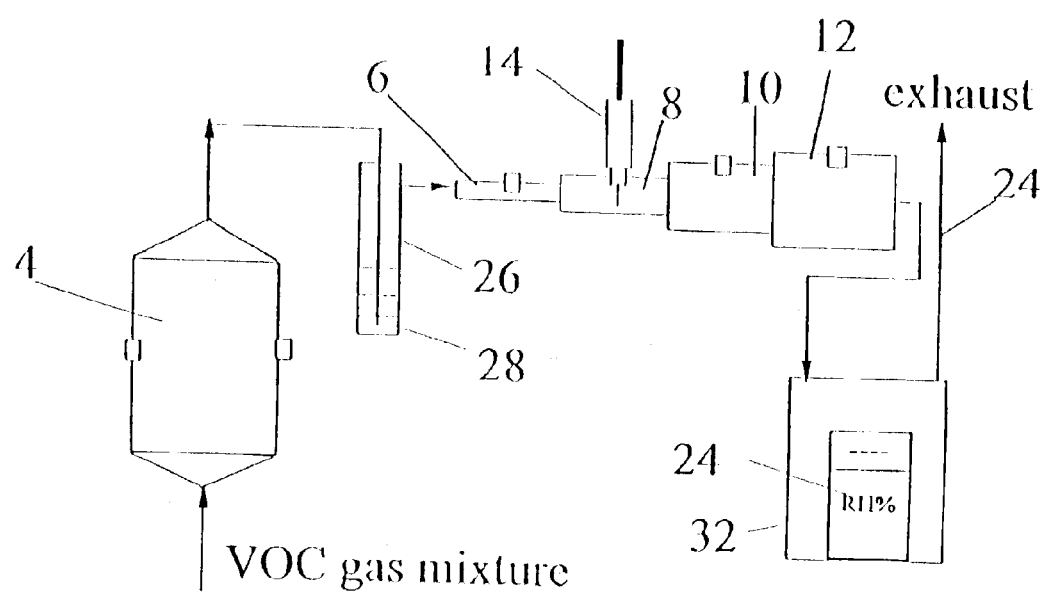
FIG. 2 is a further embodiment of an air sampling system for samples having varying humidities.

Design for Air Humidity Study. As shown in FIG. 2, to create a dynamic airflow under different humidities, an in-line impinger trap 26 (Supelco, Oakville, ON), and a humidity meter 28 (Radio Shack, Waterloo, ON) were installed in the air sampling system. The components of FIG. 2 that are identical to the components of FIG. 1 are described using the same reference numerals as those used in FIG. 1 without further description. Relative humidities of 47% and 75% were obtained by maintaining the water level in the impinger trap at 1.0 cm and 8.0 cm height, respectively. A 65 μm PDMS/DVB fiber was used to sample VOC's in the gas mixture under different humidities.

Gas Chromatography. A Varian 3400 GC (Varian Associates, Sunnyvale, Calif.), equipped with a FID and a carbon dioxide-cooled septum programmable injector, was used to analyze air samples extracted by SPME fibers and liquid samples of standard compounds. An SPB-5 capillary column (30m×0.25 mm i.d., 1.0 μm film thickness) was installed in the GC, and UHP helium was used as the carrier gas with a flow rate of 2.0 mL/min at 26 psi head pressure. The oven temperature program was 50° C. for 1 min, 15° C./min to 240° C. and held for 2 min. For SPME fiber desorption, the injector temperature was isothermally set at 300° C. for Carboxen/PDMS fibers, and at 250° C. for PDMS/DVB fibers. For liquid injection, the injector was programmed from 45° C. to 225° C. at a ramp of 300° C./min. The quantification of target VOC's in standard gases was based on the response factors obtained from the FID signals by liquid injection of VOC standards in the test range.

Figure 3:
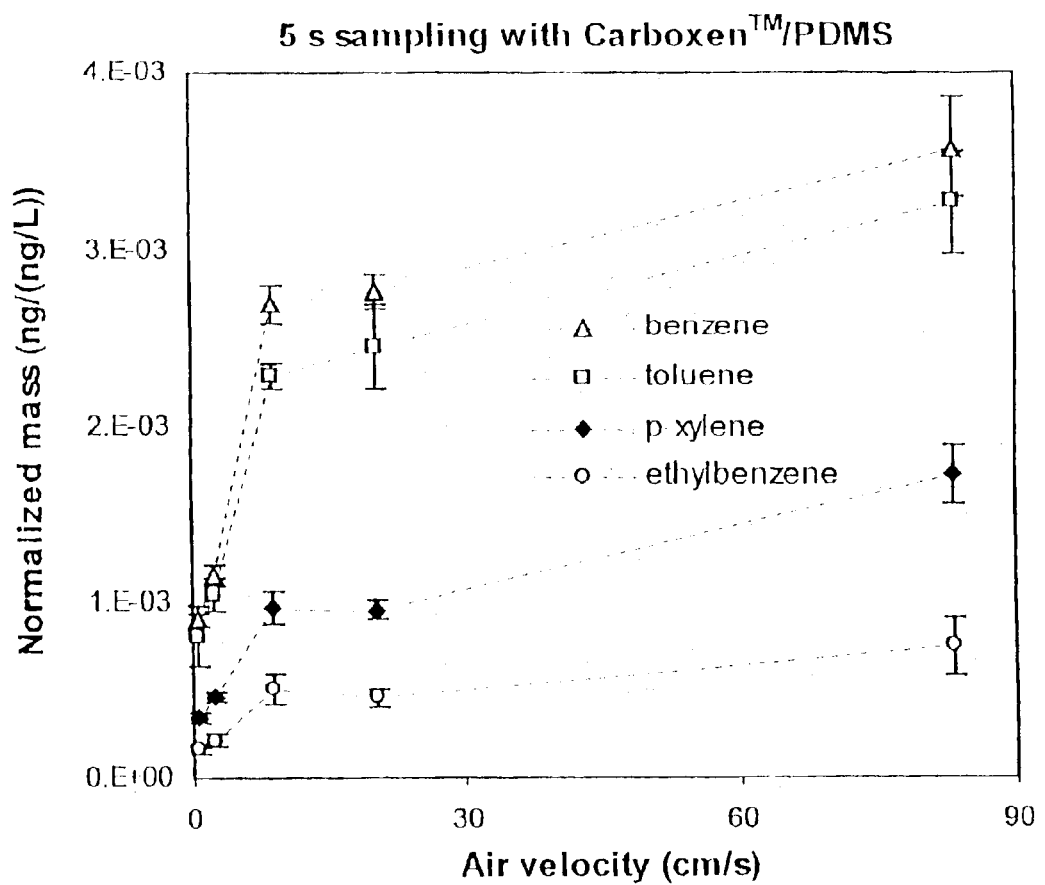
FIG. 3 is a graph showing the effect of wind velocity on adsorption.

Effects of Air Velocity. FIG. 3 shows the effect of wind velocity on the adsorption of benzene, toluene, p-xylene and ethylbenzene on a 75 micrometers Carboxen/PDMS coating for 5 s sampling of airborne BETEX. Each data point represents a normalized mass, i.e., the ratio of adsorbed mass and the analyte concentration in air, and is shown with ± one standard deviation for three samples. FIG. 3 clearly indicates that two distinct regimes of mass transfer are present: regime (1) where the extracted amount depends on the air velocity and regime (2) where the air velocity has a less significant effect on the amount of extracted mass ("semi-plateau" region).

The two zone phenomena can be explained by considering an interface between air and the porous solid sorbent. The first region in FIG. 3 describes diffusion of analytes through the static, well-developed boundary layer surrounding the SPME coating. In this region, the increase in air velocity causes a reduction in the boundary layer thickness and more of each analyte can be extracted per unit of time. This finding is consistent with the theory summarized by Equation 2. In the second region, above some critical velocity, the thickness of the boundary layer is further reduced, but it is small enough that the mass transfer is controlled by the diffusion inside the pores of the SPME coating. Therefore the increase in air velocity has only a small effect on the amount of extracted analyte.

The critical velocity for which the effects of the boundary layer thickness are negligible is approximately 10 cm/s for the analytes in this study. Although this range is lower than the average air velocities in ambient air, the critical velocity is close to the range of measured air velocities in typical indoor air. Reported average indoor air velocities at the breathing-zone height varied from 9.9 to 35.5 cm/s, with the average of 19 locations in a workroom varying from 1.4 to 9.7 cm/s. Particular care must be taken to ensure the reproducibility of extraction conditions with porous SPME fibers in field sampling. This is because a small change in air velocity in the vicinity of solid SPME fiber can have a significant effect on the amount of adsorbed analyte, particularly in the first mass transfer region (FIG. 3).

Considering the fact that the amount of extracted mass for solid SPME fibers can be enhanced when sampling is conducted at greater air velocities, i.e., in the "semi-plateau" region (FIG. 3), an external fan or an attachment to an air sampling pump can be used to provide greater rate of mass transfer. Such a device could be used by air sampling professionals wishing to equalize the extraction conditions and provide reproducible effective thickness of the boundary layer for each sample. The use of a higher air velocity for sampling with solid SPME coatings leads to enhanced sensitivity. Preliminary results indicate that the use of solid PDMS/DVB 65 $\mu$m fiber coating, 30 s sampling and average air velocity of 1 m/s allows for detection of BTEX at 10 ppt (by volume) range.

The greatest amount of mass was adsorbed for benzene, followed by toluene, p-xylene and ethylbenzene. This finding is consistent with theory presented in Equation 2, i.e., the mass of adsorbed analyte using rapid sampling is proportional to the $D_g$ for each analyte, when all other sampling conditions are equal. The 75$\mu$m Carboxen™/PDMS coating was acting as a zero sink for short sampling times. The ratio of normalized masses in FIG. 3 for benzene and toluene was close to the ratio of their $D_g$'s estimated by the FSG method. Normalized masses for ethylbenzene and p-xylene were smaller than expected. This discrepancy is likely associated with experimental errors.

Figure 4:
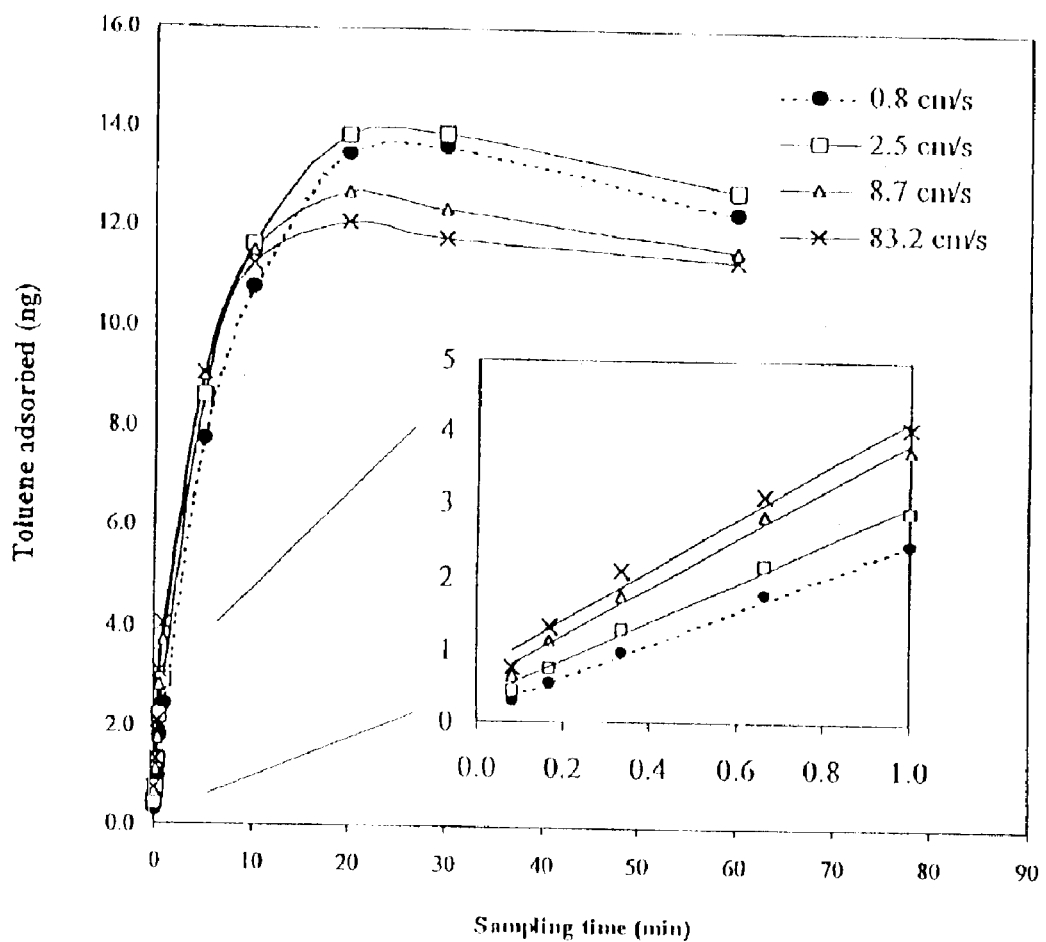
FIG. 4 is a graph showing the extraction time profiles of toluene under different wind velocities.

FIG. 4 shows the extraction time profiles of toluene using a 65 $\mu$m PDMS/DVB fiber under different wind velocities ranging from 0.8 to 83.2 cm/s. These curves illustrate the variation of toluene uptake within the whole range of indoor air wind speed. The toluene mass loading on PDMS/DVB fiber linearly increases with the sampling time within a short period of time (1 min). Furthermore, within this short sampling time, the toluene uptake rises with the increase of wind velocity. However, the equilibrium mass loading of toluene generally decreases with the increase of wind speed. This is caused by the fact that other, more strongly bound compounds extract faster as well resulting in a faster occurring displacement effect.

A further examination of the wind speed effect indicates that there are different influences on toluene adsorption on PDMS/DVB fiber when sampling at different wind velocities. Generally, the slope of the toluene extraction time profiles increases with the increase of wind velocity. If we plot the slopes of toluene extraction time profiles against the average wind velocities applied, we can obtain FIG. 5. This figure demonstrates that the slope increases approximately linearly as the wind speed increases from 0.8 to 8.7 cm/s. This means that the toluene mass loading on PDMS/DVB fiber was significantly affected by the variation within the average indoor wind velocity range (0–10 cm/s), and an approximately linear increase of mass loading can be expected within this wind range. Only a slight increase of toluene extraction was found as the wind speed increased from 8.7 to 83.2 cm/s. This range of wind velocity is usually found at indoor air ventilating zones. This indicates that the mass loading of toluene is only slightly affected by the variation of wind speed within indoor air ventilating zones (>10 cm/s).

Figure 5:
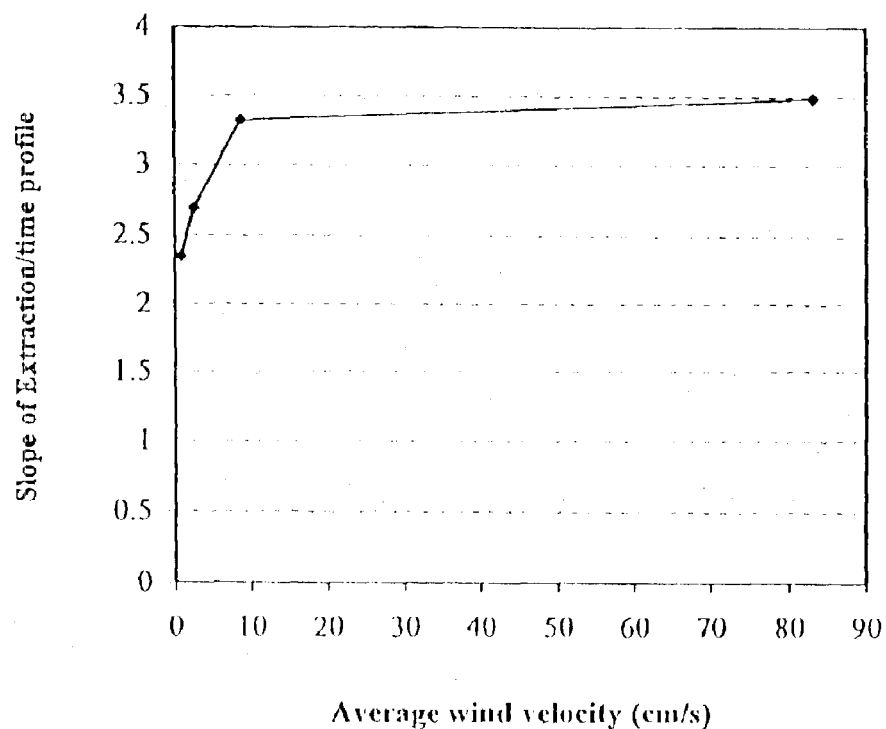
FIG. 5 is a graph of the slopes of toluene extraction time profiles and wind velocity.
Figure 6:
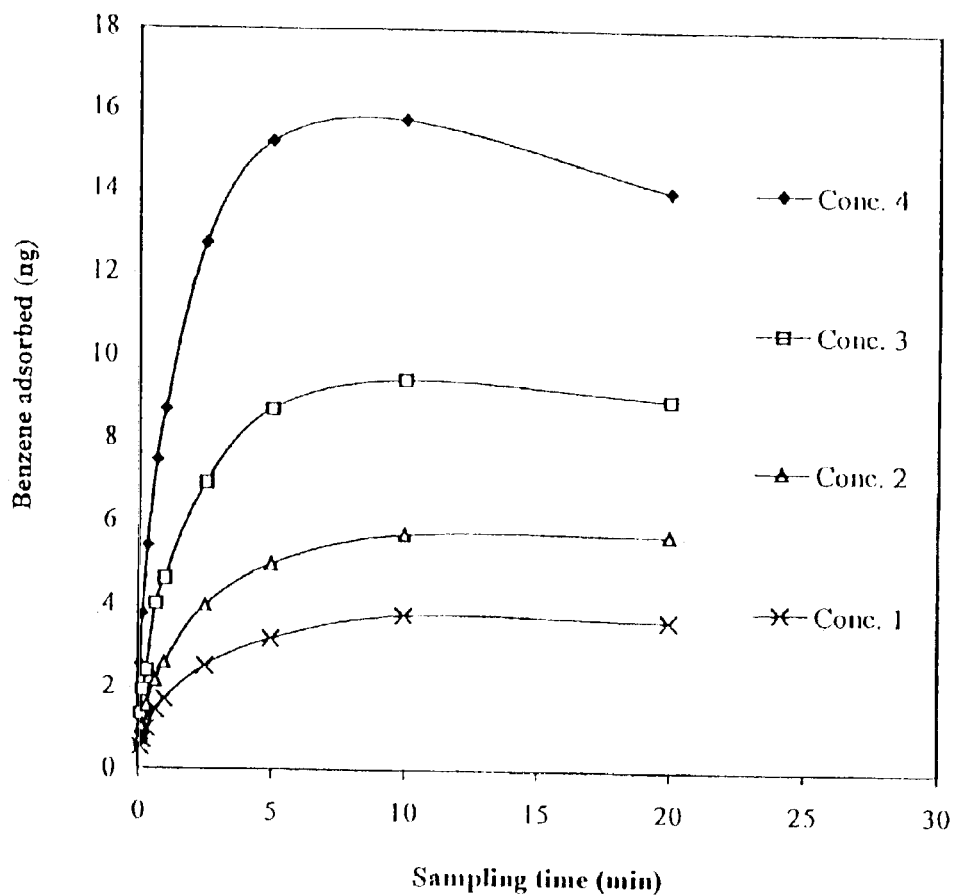
FIG. 6 shows extraction time profiles for difference concentrations of benzene at high wind velocities.
Figure 7:
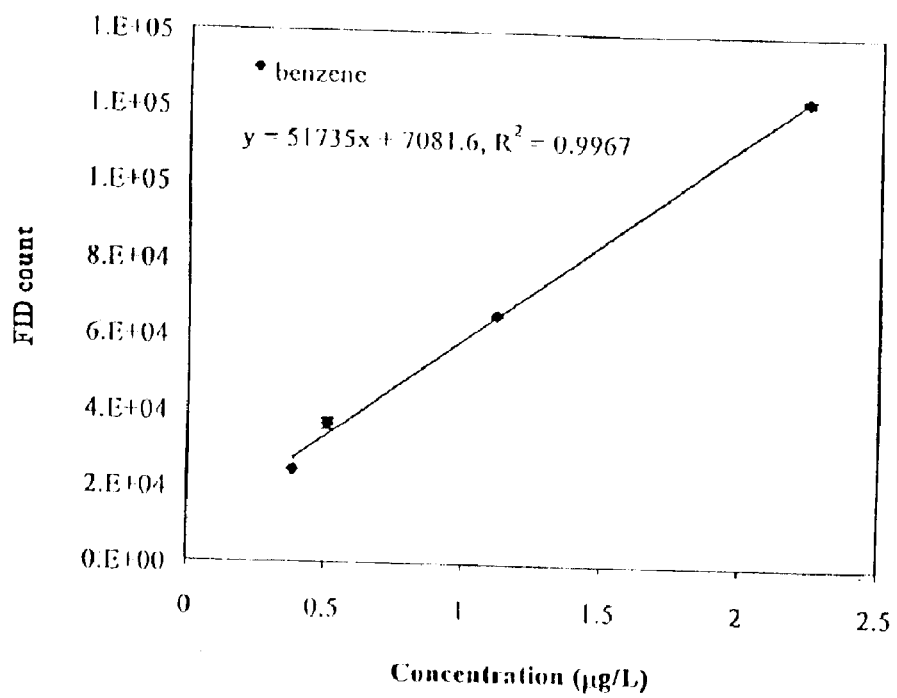
FIG. 7 is a graph of the amount of benzene adsorbed and concentration after one minute of sampling time.

Air Sampling under Wind Velocities Equal to or above a Critical Air Velocity. FIGS. 4 and 5 suggest that air sampling with a PDMS/DVB fiber should be conducted above some critical air velocity, above which the mass transfer and the analyte uptake are not affected by air velocity variation. FIG. 6 shows extraction time profiles for benzene using a 65 $\mu$m PDMS/DVB fiber to sample a standard VOC gas mixture at wind velocities equal to or above 10.2 cm/s. Three VOC concentrations were obtained by setting different incubation temperatures (35, 40 and 60° C.) for VOC permeation tubes and a constant air flow at 2,000 sccm. Another VOC concentration was generated by maintaining the incubation temperature at 60° C. and increasing the air flow rate to 4,000 sccm. These curves illustrate that the benzene uptake increased with the sampling time before reaching its equilibrium level. The higher the concentration, the less time was required for the PDMS/DVB fiber to reach the equilibrium. However, only within a very short sampling time (1 min), was benzene mass loading approximately linear with sampling time. FIG. 7 shows that benzene uptake or response increased linearly with the concentration when 1 min sampling time was used under an air velocity equal to or above 10.2 cm/s. For other target VOC's, i.e., toluene and p-xylene, similar results were also observed (data not shown).

Figure 8:
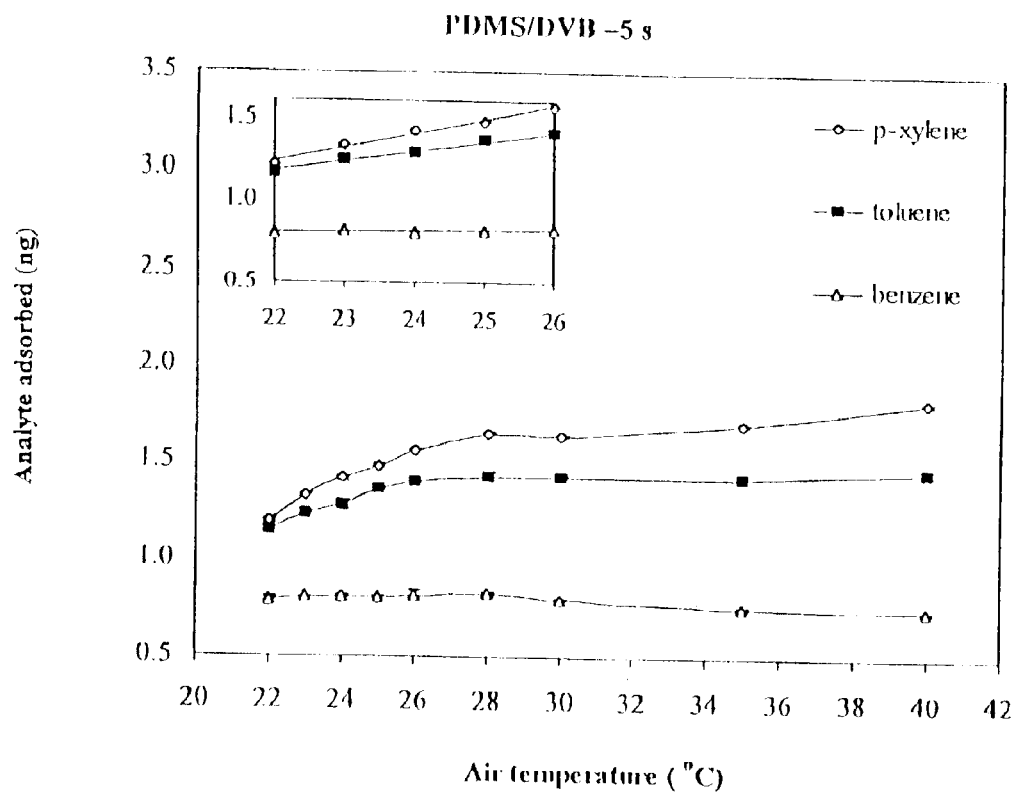
FIG. 8 is a graph of the amount of adsorption with temperature.
Figure 9:
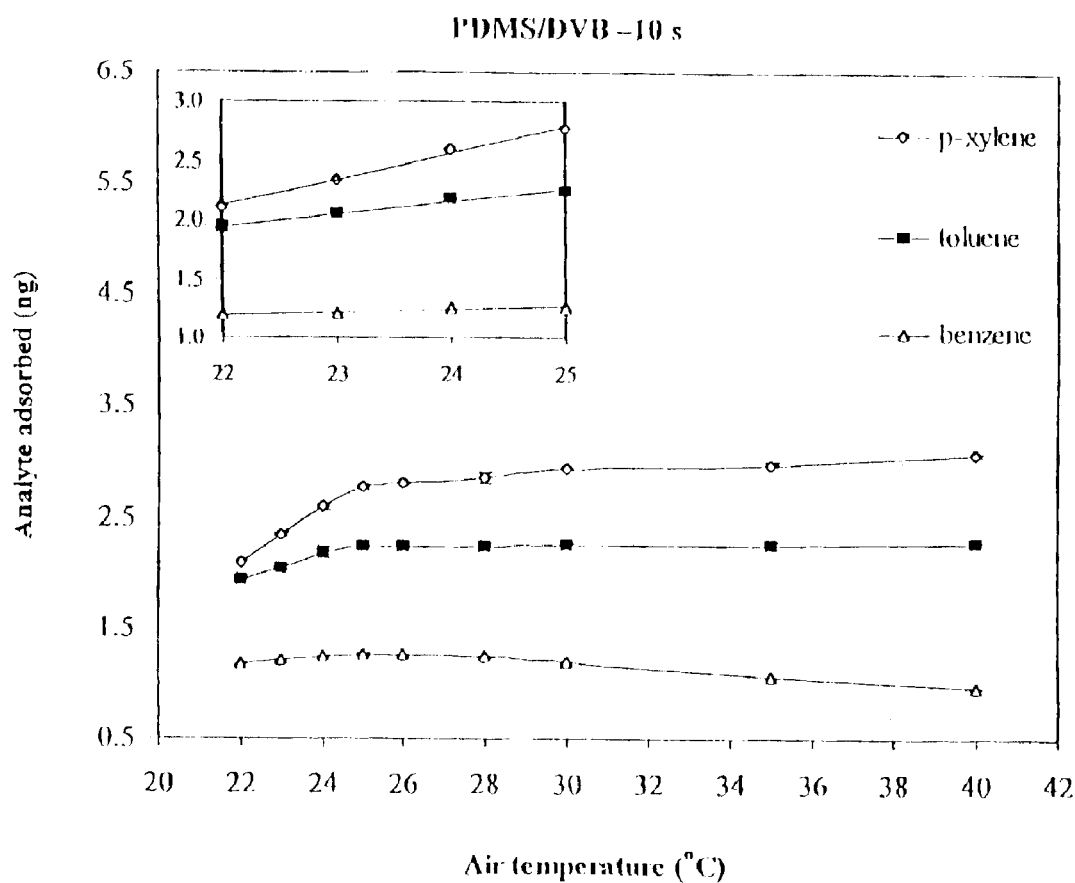
FIG. 9 is a graph showing the relationship between the amount adsorbed at an exposure time of 5 seconds with increasing temperature.

Temperature Effect on VOC Adsorption on Porous SPME Fibers. FIG. 8 shows that amounts of toluene and p-xylene adsorbed on the PDMS/DVB fiber for a 5 s exposure increase linearly as the temperature increases from 22 to 26° C., while benzene uptake remains almost constant in this temperature range. As the temperature increases continuously, the amounts of toluene and p-xylene adsorbed increase slightly, while the amount of benzene adsorbed decreases. This indicates the displacement of benzene molecules by p-xylene or toluene molecules, which have higher affinities to the PDMS/DVB coating than benzene. The results indicate that increasing temperature within a certain range will enhance the adsorption of VOC's on PDMS/DVB coating, especially for analytes with higher affinity to the coating. Similarly to FIG. 8, FIG. 9 shows that the mass of toluene and p-xylene adsorbed onto the PDMS/DVB fiber for a 10 s exposure increase with the increase of temperature from 22 to 25° C. Benzene adsorbed remains almost constant from 22 to 25° C., but decreases as the temperature increases further from 25 to 40° C. In fact, this situation should be expected because the active surface sites become saturated as the adsorption on the coating proceeds, and some benzene molecules are possibly displaced by toluene or p-xylene molecules.

Figure 10:
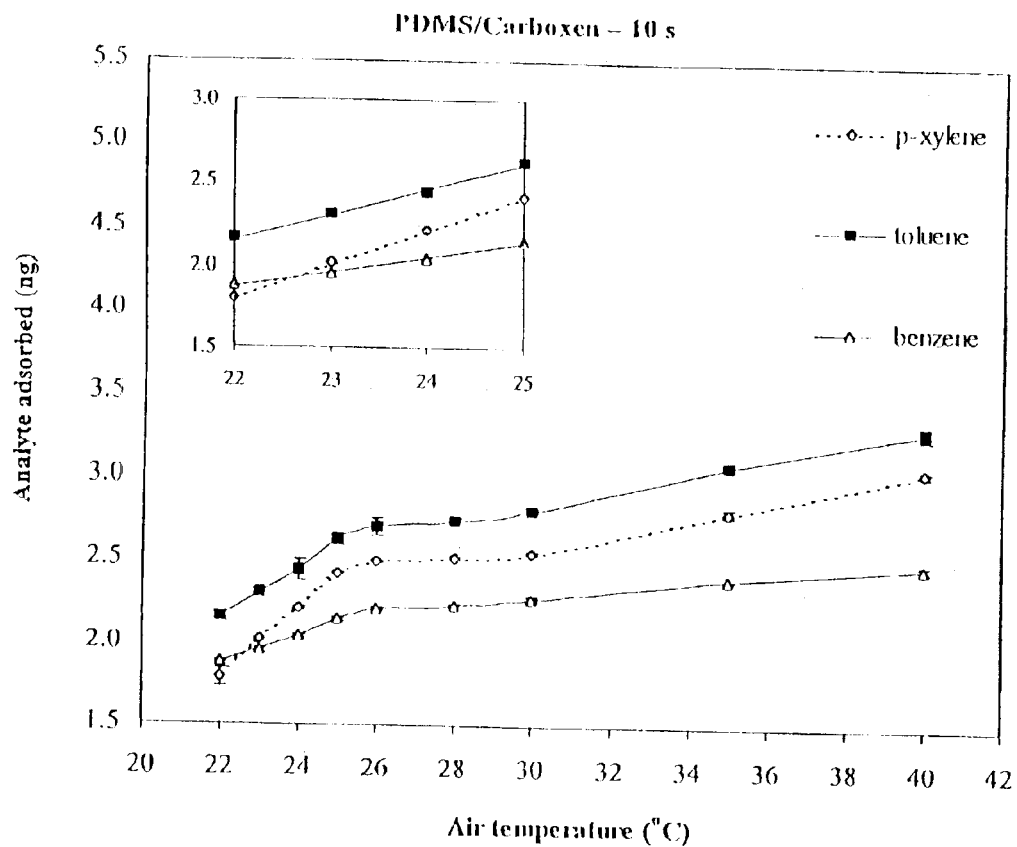
FIG. 10 is a graph showing the amount of adsorption with temperature at a 10 second sampling time with a different fiber than that used for FIG. 9.

In FIG. 10, amounts of all three analytes adsorbed on the Carboxen/PDMS fiber increase linearly as the temperature increases from 22 to 25° C. when using 10 s sampling time.

As the temperature increases continuously, the mass of analytes adsorbed only increases slightly. Generally, a similar adsorption behavior between PDMS/DVB and Carboxen/PDMS was observed. However, the Carboxen/PDMS fiber has a higher adsorption capacity than PDMS/DVB fiber for extraction of benzene, the smallest molecule among the analytes. Unlike the DVB particle consisting of mainly mesopores and a smaller fraction of macropores and micropores, the Carboxen polymer particle has an even distribution of micro, meso, and macro pores. Therefore, Carboxen particles are better for sampling smaller molecules ($C_2$–$C_{12}$) compared to PDMS/DVB fiber. Unfortunately, the weakness of Carboxen/PDMS is the difficulty for analyte desorption. Peak tailing is often observed even with the GC injector temperature of 300° C.

As one of the most important experimental parameters in SPME sampling, the extraction temperature has been discussed in several previous papers related to SPME air sampling. When a pure-phase liquid SPME fiber is used, an increase in extraction temperature usually causes an increase in extraction rate, but simultaneously a decrease in the distribution constant. Since the extraction by the SPME coating is an exothermic process, a decrease in mass loading at equilibrium is usually expected as the extraction temperature increases. In contrast to liquid fiber, however, an opposite trend of temperature effect was found in this study when mixed-phase porous SPME fibers were used. Within a very short sampling time (far from equilibrium), VOC analytes on a porous SPME fibre can linearly increase as the extraction temperature increases in a narrow range. Since VOC adsorption on a porous SPME fiber is controlled by the diffusion process or diffusion coefficient rather than the extraction equilibrium or distribution constant, an increase in diffusion coefficients with an elevated temperature should increase VOC uptake on the solid SPME coating.

Figure 11:
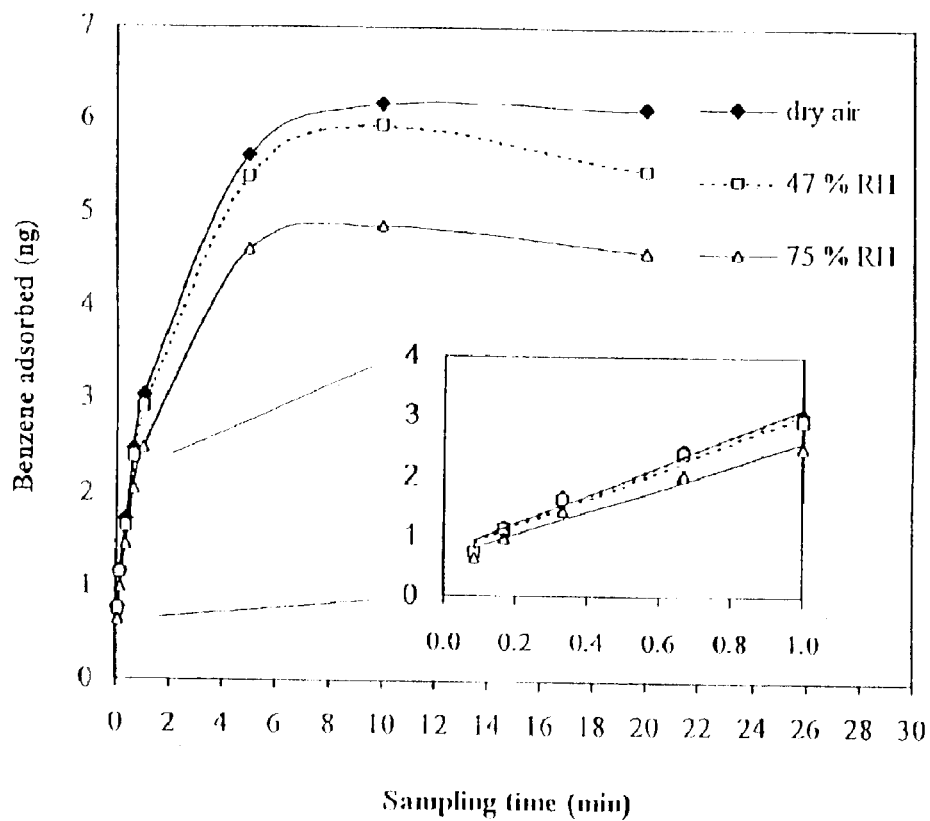
FIG. 11 is a graph showing the amount of benzene adsorbed with time at different humidities.
Figure 12:
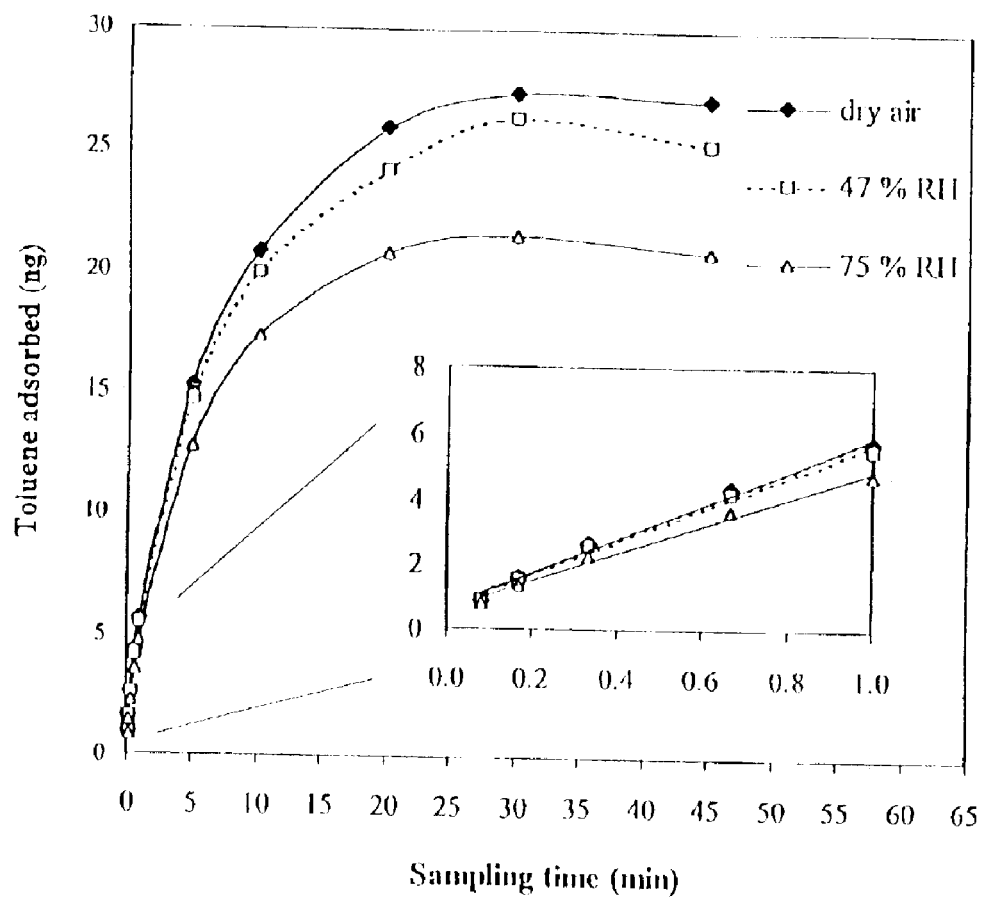
FIG. 12 is a graph showing the amount of toluene adsorbed with time at different humidities.
Figure 13:
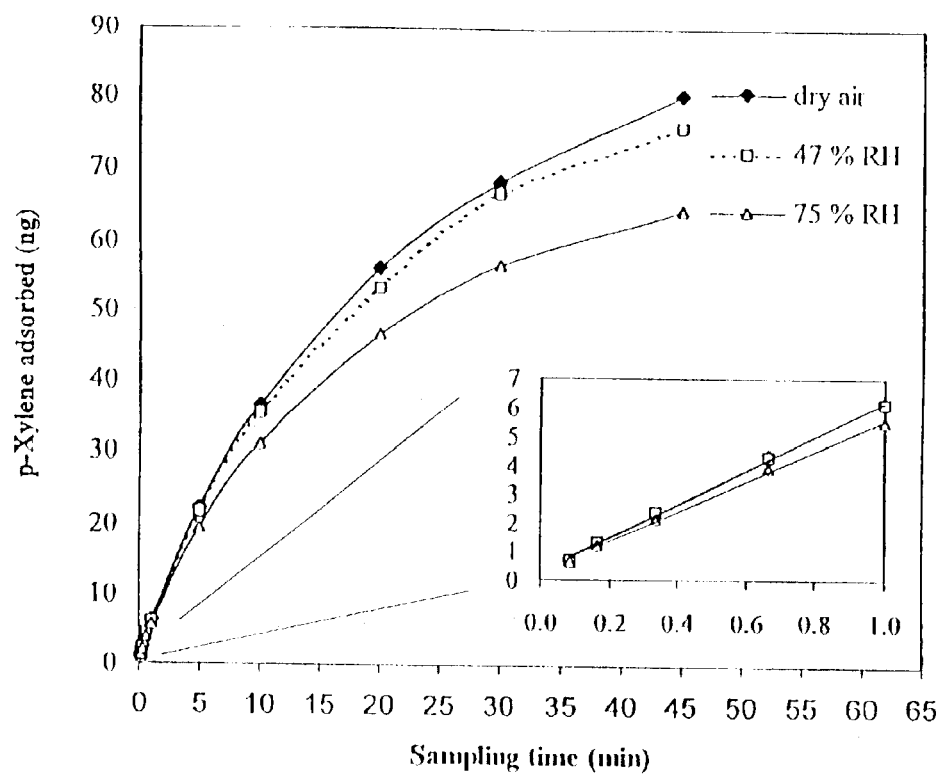
FIG. 13 is a graph showing the amount of p-Xylene adsorbed with time at different humidities.

Effect of Humidity on VOC Adsorption onto PDMS/DVB Fiber. FIGS. 11–13 are the extraction time profiles of benzene, toluene and p-xylene using a 65 µm PDMS/DVB fiber to extract a standard VOC gas mixture at different humidities. These figures indicate that a humidity level of 75% resulted in a significant decrease in the VOC uptake on the PDMS/DVB coating at equilibrium, especially for smaller molecules, e.g., benzene. Due to the high affinity to the PDMS/DVB porous polymer coating, water molecules compete with other VOC molecules and occupy a portion of active surface sites on the coating surface. Therefore, fewer active surface sites are available to VOC molecules, especially to smaller molecules with lower affinity to the coating. However, within a very short sampling time, i.e., 1 minute, no significant difference was observed among the conditions with different humidities. This indicates that the active surface sites are not saturated within a very short extraction time, and still available to VOC molecules. Thus, a short sampling time (far before equilibrium) minimizes the effect of humidity on adsorption of VOC's on the PDMS/DVB coating. Table 4 shows the effect of relative humidity for decreasing VOC uptake onto the PDMS/DVB coating. The humidity effect can be neglected if using PDMS/DVB fiber for a very short time air sampling in a low humidity (<50%). However, the result suggests that a mass loading decrease of VOC on PDMS/DVB can be expected if the relative humidity is above 50%.

Air wind velocity and temperature are important parameters related to the diffusion process on porous polymer SPME fibers, particularly at non-equilibrium conditions. Wind speed or bulk air movement significantly affects the VOC mass transfer process from the bulk air to the fiber in a certain range. This indicates that the thickness of the gas-phase boundary layer between the fiber and air is diminished as the wind speed increases, and the mass transfer rate was accelerated between 0 and 5 cm/s. This wind speed range is typical to average air velocities in indoor air. Therefore, air sampling with porous polymer coated SPME fibers should be conducted above some critical air velocity, above which the mass transfer and the analyte uptake are not affected, and the extraction can be reproduced.

Figure 14:
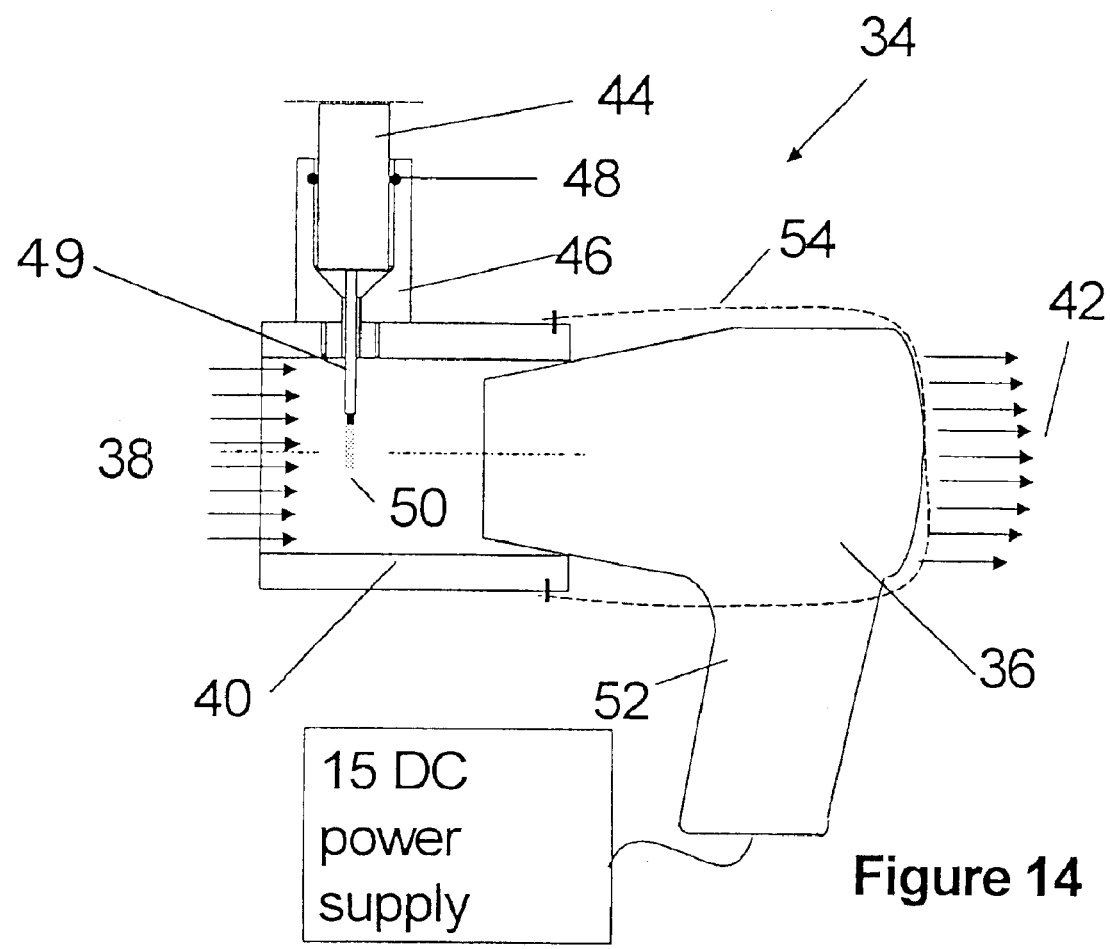
FIG. 14 shows an extraction device having an electric blower to provide constant air agitation.

When using a liquid SPME fiber, a decrease in mass loading at equilibrium is usually expected as the extraction temperature increases because the extraction is an exothermic process. An opposite trend of temperature effect was found in this study when mixed-phase porous SPME fibers were used with a short sampling time. Within a very short sampling time far from equilibrium, analytes extracted on a porous polymer coated SPME fiber increased linearly as the extraction temperature increased in a narrow range from 22 to 25° C. In this case, the adsorption process is controlled by diffusion coefficients instead of distribution constants of analytes. The effects of wind and temperature on adsorption by porous polymer coated SPME fibers under non-equilibrium conditions have not been addressed by previous researchers. The analytical data indicate that there is a direct relationship between the rate of mass transfer and the analyte diffusion coefficients. Therefore appropriate diffusion coefficients obtained either from the literature, calculated or experimentally determined can be used to calibrate the relationship between amount of analyte extracted versus concentration for given extraction time. During the experiment constant agitation condition are necessary, or if different agitation conditions are used than the appropriate adjustment coefficients needs to be calculated. FIG. 14 shows the example of a simple device 34 based on an electric blower 36 having a fan (not shown) that sucks air into an inlet 38 on a cylindrical head 40 and exhausts the air through an outlet 42. The flower 36 is able to provide constant air agitation. An SPME device 14 has a holder 44 mounted in an SPME insert 46. An O ring 48 is located between the holder 44 and insert 46. A sleeve 49 extends through the head 40 to position a fiber 50 within the head 40. The blower 36 has a handle 52. The reported data can be extended to liquid sample analysis. In this case, diffusion of analytes in a liquid matrix can be used to calibrate the response. Analogous devices to one showed on FIG. 14 for air analysis can be designed to provide constant agitation of the sample matrix. For solid samples, indirect headspace or liquid extraction can be used.

For air analysis, high humidity was found to decrease VOC uptake on the PDMS/DVB coating. However, the humidity effect can be minimized by using a very short exposure time, in which case the active surface sites are not saturated. The humidity effect can be neglected when using PDMS/DVB fiber for a very short time air-sampling in a low humidity, but a mass loading decrease of VOC's on PDMS/DVB can be expected if air samples are taken from a high humidity environment when the calibration might be necessary. It is expected that both temperature and humidity will be monitored during the field measurement and appropriate correction coefficients will be calculated, if necessary to adjust the response.

The proposed diffusion based extraction and calibration approach is expected to be the fastest possible sampling/sample preparation approach in the field and in the laboratory. Various different arrangements of the extraction phase can be used to practically implement this technology (see FIGS. 15A to 15E).

In FIG. 15A, a vessel 60 containing a sample 62 has an extraction phase coating 63 on a tubular member 64. In FIG. 15B a tube 66 has an extraction phase coating 63 on an inner surface thereof. Sample 62 contacts the extraction phase coating as it flows through the tube 66.

In FIG. 15C, the vessel 60 has an extraction phase coating 63 lining an inner surface thereof. The sample 62 contacts the coating 63 when it is contained in the vessel.

In FIG. 15D, the vessel 60 contains the sample 62. Particles 72 are located within the sample and each particle is surrounded by extraction phase coating 63. In FIG. 15E, the vessel 60 has a sample 62 with a stirrer 74 extending into the sample. The stirrer has paddles 76 with extraction phase coating 63 on the paddles. In FIG. 15F, there is shown a vessel 60 containing a sample 62 with a stirring bar 78 located within the sample. The stirring bar 78 contains extraction phase coating 63.

Figure 16:
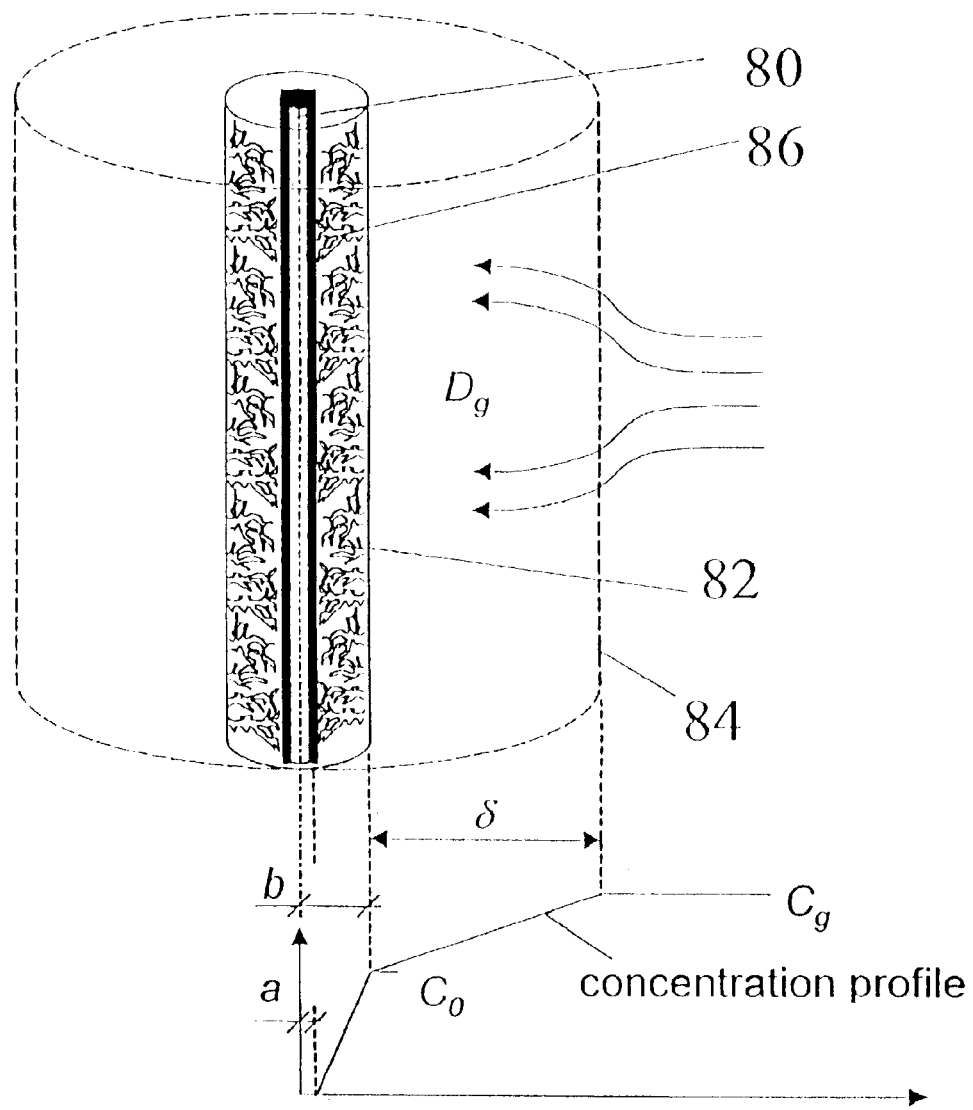
FIG. 16 is a schematic perspective view of a boundary layer surrounding a silica rod having an extraction coating thereon and a graph of concentration profile.

In FIG. 16, there is shown a schematic perspective view of a silica rod 60 surrounded by a solid extraction phase coating 82 that is porous and contains pores 86. A cylindrically shaped boundary layer 84 surrounds the cylindrically shaped coating 82 and analytes, designated by $D_g$, pass through the boundary layer and are adsorbed by the coating 86. A graph at the bottom of FIG. 16 shows that the boundary layer has a thickness delta, the rod 80 has a radius a and a radius b equals the distance from a center of the rod 80 to the exterior surface of the coating 86. The concentration at $C_o$ is the concentration at the interface between the boundary layer and the coating and the concentration at $C_g$ is the concentration of the gas.

Figure 17:
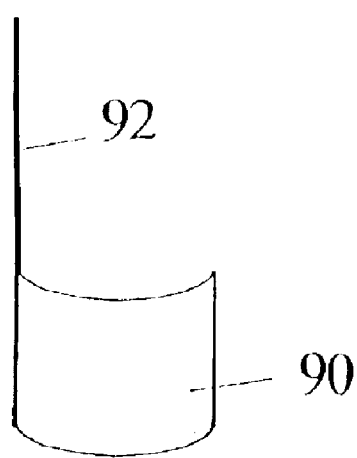
FIG. 17 is a perspective view of an expanded membrane attached to a handle.
Figure 18:
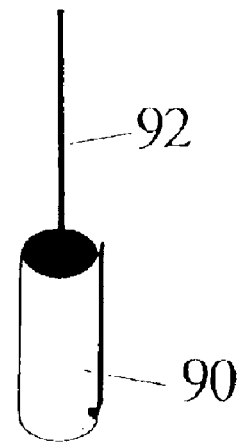
FIG. 18 is a perspective view of the membrane of FIG. 17 rolled around the handle.

In FIG. 17, a membrane 90 is supported on a handle 92 and the membrane is in an unfolded position. In FIG. 18, the membrane 90 is rolled around the handle 92. FIG. 17 shows the collection mode where the handle and membrane are brought into contact with a sample (not shown). After rapid extraction has occurred, the membrane is moved out of contact with the sample and the membrane 90 is rolled around the handle 92 to make it more compact. The membrane and handle can then be inserted into a cylindrical sheath (not shown), which is airtight. The membrane can then be transferred to an analytical instrument, which can be located in the field where the sample has been taken or to an instrument located away from the test site. The sheath prevents the membrane from becoming contaminated during transport.

Figure 19:
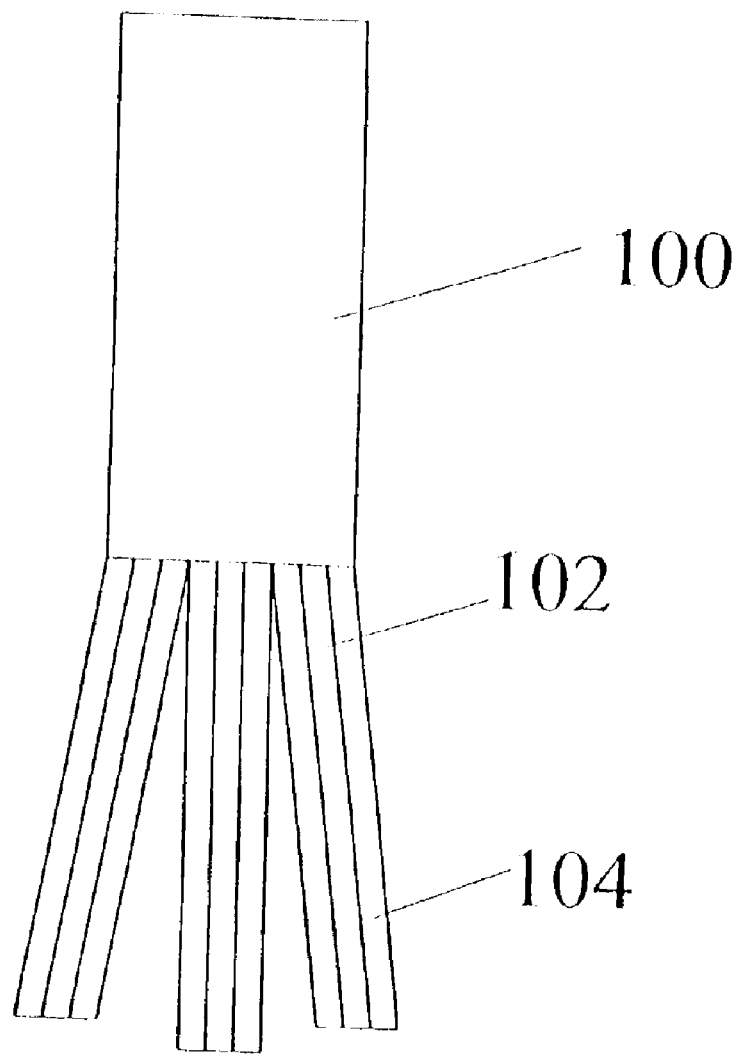
FIG. 19 is a schematic side view of a holder having three fibers.
Figure 20:
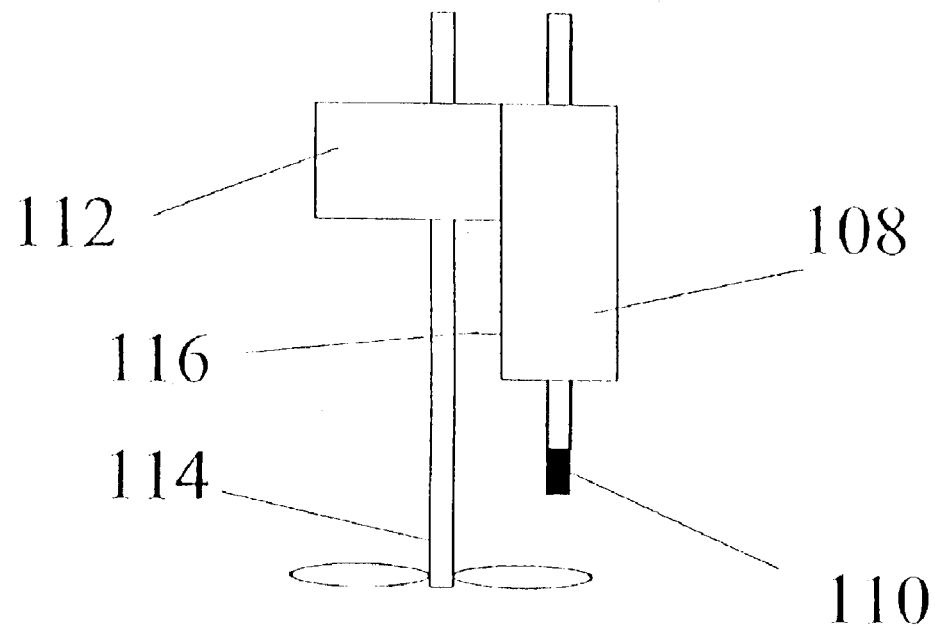
FIG. 20 is a schematic side view of a device for determining the concentration of analytes in a liquid.

In FIG. 19, there is shown a further embodiment of the invention where a brush 100 has bristles 102 extending therefrom and each bristle has an extraction phase coating 104 thereon. In FIG. 20, a device 107 has a SPME syringe 108 supporting a fibre 109 with a coating 110. A motor 112 powers a stirrer 114 in a bracket 116.

I claim:

1. A method of determining the concentration of analytes of interest in a sample using a solid phase microextraction device having a surface containing an extraction coating, said method comprising bringing said sample into direct contact with said coating while highly agitating said sample under controlled conditions to maintain a substantially constant boundary layer between said sample and said coating, limiting a time of contact between said sample and said coating so that all analytes that pass through said boundary layer are adsorbed, terminating said contact and determining the amount of each analyte of interest in said coating and calculating the concentration of the analytes of interest in said sample by using the diffusion coefficient for said analytes and said amount in said coating.

2. A method as claimed in claim 1 including the step of limiting the time of said direct contact between said sample and said coating to a range of a few seconds to substantially two minutes.

3. A method as chimed in claim 2 including the step of limiting the time of said direct contact to substantially one minute.

4. A method as claimed in claim 2 including the step of limiting the time of said direct contact to substantially ten seconds.

5. A method as claimed in claim 2 including the step of sizing the coating to be much larger than the maximum coating required to adsorb all of the analytes that pass through said boundary layer within the time of said direct contact.

6. A method as claimed in claim 1 including the step of selecting said surface from the group of a fiber, a tube, an interior surface of a vessel, suspended particles, a stirrer and a stirring bar and a disk.

7. A method as claimed in claim 6 wherein the surface is a fiber and said method includes the step of highly agitating said sample by vibrating said fiber.

8. A method as claimed in claim 6 wherein the surface is a tube and the method includes the step of highly agitating said sample by forcing said sample through said tube.

9. A method as claimed in claim 6 wherein the sample is located in a vessel and the surface is an interior surface of said vessel, said method including the step of highly agitating said sample by vibrating said vessel.

10. A method as claimed in claim 6 wherein said surface is a surface of said suspended particles, said method comprising highly agitating said sample by vibrating or shaking said vessel.

11. A method as claimed in claim 6 wherein said vessel contains a stirrer, said stirrer having paddles with said extraction coating located thereon, said method comprising highly agitating said sample by activating said stirrer.

12. A method as claimed in claim 6 wherein said vessel contains a stirrer, said method comprising highly agitating said sample by activating said stirrer.

13. A method as claimed in claim 6 wherein a vessel contains a stirring bar, a surface of the stirring bar being the surface that has the extraction coating thereon, said stirring bar having an extraction coaxing thereon, said method comprising highly agitating said sample by activating said stirring bar.

14. A method as claimed in claim 6 including a step of controlling the agitation by maintaining said agitation conditions at a substantially constant level.

15. A method as claimed in claim 1 including the steps of controlling the agitation conditions to vary the degree of agitation, correlating the degree of agitation with the amount of extraction and determining the concentration of analytes of interest by adjusting for the degree of agitation.

16. A method as claimed in claim 1 including the step of desorbing said analytes from said coating by inserting said coating into an injection port of a suitable analytical instrument.

17. A method as claimed in claim 2 wherein said sample contains particulates and said method includes the steps of accumulating particulates on said surface and using one of Raman spectroscopy and x-ray fluorescence to characterize the accumulated particulates.

18. A method as claimed in claim 1 including the step of creating a well-defined artificial boundary layer by using a polymeric membrane that covers said surface containing said extraction coating.

19. A method as claimed in claim 1 including the step of desorbing analytes from said coating by placing said coating into an injection port of an analytical instrument and carrying out desorption and analysis.

20. A method as claimed in claim 1 including the steps of choosing the coating to be a mixed phase coating.

21. A method as claimed in claim 20 including the step of choosing the coating from the group of PDMS/DVB, Carboxen/PDMS and Carbowax/DVB.

22. A method as claimed in claim 1 including the step of choosing the coating to be a solid, liquid, inorganic or organic coating including molecular imprinted polymers (MIP's), antibodies and polypyrroles.

23. A method as claimed in claim 1 including the step of choosing the coating to selectively extract analytes of interest from the sample.

24. A method as claimed in claim 1 including the steps of collecting the analytes in the field using a portable device, sealing the analytes collected and returning to a location that has an analytical instrument, desorbing the analytes collected into the instrument.

25. A method as claimed in claim 1 including the steps of carrying out extraction for a limited time that is far short of the extraction time required to reach equilibrium.

26. A method as claimed in claim 1 including the step of determining the concentration of analytes of interest in at least one of said coating and said membrane by desorbing said analytes of interest into an analytical instrument.

* * * * *